US012048469B2

United States Patent
Fan et al.

(10) Patent No.: US 12,048,469 B2
(45) Date of Patent: Jul. 30, 2024

(54) CRYOSPRAY CATHETERS

(71) Applicant: CSA MEDICAL, INC., Baltimore, MD (US)

(72) Inventors: Wei Li Fan, Malden, MA (US); Rafael Cordero, Bedford, MA (US); Stephen Griffin, San Jose, CA (US); Benedict Shia, Needham, MA (US); Sergei Babko-Malyi, Winchester, MA (US); Stephen M. McCartin, Chelmsford, MA (US); Brian M. Hanley, Reading, MA (US)

(73) Assignee: CSA MEDICAL, INC., Lexington, MA (US)

( * ) Notice: Subject to any disclaimer, the term of this patent is extended or adjusted under 35 U.S.C. 154(b) by 489 days.

(21) Appl. No.: 14/012,320

(22) Filed: Aug. 28, 2013

(65) Prior Publication Data
US 2015/0066005 A1   Mar. 5, 2015

Related U.S. Application Data

(63) Continuation-in-part of application No. 13/784,596, filed on Mar. 4, 2013, now Pat. No. 9,144,449.

(51) Int. Cl.
*A61B 18/02* (2006.01)
*A61B 18/00* (2006.01)

(52) U.S. Cl.
CPC ...... *A61B 18/0218* (2013.01); *A61B 2018/00541* (2013.01); *A61B 2018/00577* (2013.01); *A61B 2018/0212* (2013.01)

(58) Field of Classification Search
CPC .......... A61B 2018/00029; A61B 2018/00035; A61B 18/0218
See application file for complete search history.

(56) References Cited

U.S. PATENT DOCUMENTS 3,630,203 A   12/1971   Sellinger et al.
3,782,386 A   1/1974   Barger et al.
(Continued)

FOREIGN PATENT DOCUMENTS

DE   102017130107 A1   6/2019
EP   1089780 A1   4/2001
(Continued)

OTHER PUBLICATIONS

TJ Lynch, Polyimide Tubing: Dispelling the Myths, Microlumen, http://www.microlumen.com/news/industry-news/18-polyimide-tubing-dispelling-the-myths.*
(Continued)

*Primary Examiner* — Joanne M Rodden
*Assistant Examiner* — Bo Ouyang
(74) *Attorney, Agent, or Firm* — GOODWIN PROCTER LLP

(57) ABSTRACT

A cryosurgery system for application of medical-grade liquid nitrogen to a treatment area via a small, low pressure, open tipped catheter. The system includes a console, including a touch panel computer, a cryogen module, a suction module and an electronics module, and a disposable spray kit. Features include optional low cryogen flow setting to reduce the cryogen flow rate by 50%, improved cryogen flow consistency reducing pressure pulses and peaks, an integrated suction pump for improved consistency and self-checks, specified vent tube areas and corresponding maximum expected pressures during cryospray procedure; optional pressure sensing capability to monitor pressure during a treatment, and novel catheter designs of multilayer and flexible construction providing a variety of spray patterns.

43 Claims, 22 Drawing Sheets

(56) References Cited

U.S. PATENT DOCUMENTS

| | | | |
|---|---|---|---|
| 4,146,030 A | 3/1979 | Holroyd | |
| 5,720,764 A * | 2/1998 | Naderlinger | A61F 2/01 606/127 |
| 5,846,235 A | 12/1998 | Pasricha et al. | |
| 6,027,499 A | 2/2000 | Johnston et al. | |
| 6,143,013 A | 11/2000 | Samson et al. | |
| 6,237,355 B1 * | 5/2001 | Li | A61B 18/02 62/114 |
| 6,287,304 B1 | 9/2001 | Eggers et al. | |
| 6,306,129 B1 * | 10/2001 | Little | A61B 18/02 128/DIG. 27 |
| 6,319,248 B1 | 11/2001 | Nahon | |
| 6,413,255 B1 | 7/2002 | Stern | |
| 6,464,716 B1 * | 10/2002 | Dobak, III | A61B 18/02 606/21 |
| 6,468,268 B1 | 10/2002 | Abboud et al. | |
| 6,551,309 B1 | 4/2003 | LePivert | |
| 6,887,234 B2 | 5/2005 | Abboud et al. | |
| 7,025,762 B2 | 4/2006 | Johnston et al. | |
| 7,331,948 B2 | 2/2008 | Skarda | |
| 7,507,233 B2 | 3/2009 | Littrup et al. | |
| 7,594,925 B2 | 9/2009 | Danek et al. | |
| 7,785,289 B2 | 8/2010 | Rios et al. | |
| 7,995,816 B2 | 8/2011 | Roger et al. | |
| 8,322,335 B2 | 12/2012 | Barry et al. | |
| 9,144,449 B2 | 9/2015 | Burr et al. | |
| 9,226,648 B2 * | 1/2016 | Saadat | A61B 1/00135 |
| 2002/0143323 A1 * | 10/2002 | Johnston | A61B 18/0218 606/21 |
| 2004/0024392 A1 * | 2/2004 | Lewis | A61B 18/02 606/22 |
| 2005/0027289 A1 * | 2/2005 | Castellano | A61B 18/02 606/22 |
| 2005/0081541 A1 | 4/2005 | Copping | |
| 2005/0261674 A1 * | 11/2005 | Nobis | A61B 1/00073 606/45 |
| 2005/0283136 A1 | 12/2005 | Skarda | |
| 2006/0062895 A1 | 3/2006 | Pursley | |
| 2006/0138177 A1 | 6/2006 | Wauters et al. | |
| 2006/0200076 A1 | 9/2006 | Gonzalez et al. | |
| 2007/0123852 A1 * | 5/2007 | Deem | A61B 18/1492 606/45 |
| 2007/0123958 A1 | 5/2007 | Laufer | |
| 2007/0156125 A1 | 7/2007 | Delonzor | |
| 2007/0177008 A1 | 8/2007 | Bayer et al. | |
| 2007/0233055 A1 | 10/2007 | Abboud et al. | |
| 2007/0253463 A1 | 11/2007 | Perry et al. | |
| 2008/0312644 A1 * | 12/2008 | Fourkas | A61B 18/02 606/22 |
| 2009/0078875 A1 | 3/2009 | Rousso et al. | |
| 2009/0299356 A1 | 5/2009 | Watson | |
| 2009/0143640 A1 * | 6/2009 | Saadat | A61B 1/00089 600/104 |
| 2009/0157002 A1 | 6/2009 | Dumot et al. | |
| 2009/0192505 A1 | 7/2009 | Askew et al. | |
| 2009/0209943 A1 | 8/2009 | Marsman | |
| 2010/0042087 A1 | 2/2010 | Goldboss et al. | |
| 2010/0057065 A1 | 3/2010 | Krimsky | |
| 2010/0057067 A1 | 3/2010 | Baust et al. | |
| 2010/0081971 A1 | 4/2010 | Allison | |
| 2010/0191232 A1 * | 7/2010 | Boveda | A61B 18/14 606/33 |
| 2010/0249765 A1 | 9/2010 | Johnston | |
| 2010/0324483 A1 | 12/2010 | Rozenberg et al. | |
| 2011/0106074 A1 | 5/2011 | Kunis et al. | |
| 2011/0144524 A1 | 6/2011 | Fish et al. | |
| 2011/0208166 A1 | 8/2011 | Dumot et al. | |
| 2011/0306958 A1 | 12/2011 | Berzak et al. | |
| 2012/0015587 A1 | 1/2012 | Leishman et al. | |
| 2012/0035601 A1 | 2/2012 | Wittenberger | |
| 2013/0110098 A1 | 5/2013 | Lalonde | |
| 2013/0204068 A1 * | 8/2013 | Gnanashanmugam | A61N 5/1002 600/1 |
| 2013/0211393 A1 | 8/2013 | Barry et al. | |
| 2013/0218149 A1 * | 8/2013 | Braun | A61B 1/00082 606/21 |
| 2013/0231651 A1 | 9/2013 | Burr et al. | |
| 2014/0018788 A1 * | 1/2014 | Engelman | A61B 18/18 606/33 |
| 2015/0009460 A1 | 1/2015 | Jang et al. | |
| 2015/0066005 A1 | 3/2015 | Fan et al. | |
| 2015/0094607 A1 | 4/2015 | Barry et al. | |
| 2015/0097129 A1 | 4/2015 | Ben-Ami | |
| 2015/0119868 A1 | 4/2015 | Lalonde et al. | |
| 2015/0202003 A1 | 7/2015 | Wolf et al. | |
| 2015/0250524 A1 | 9/2015 | Moriarty et al. | |
| 2016/0125161 A1 | 5/2016 | Sankaran et al. | |
| 2017/0119258 A1 | 5/2017 | Kotanko et al. | |
| 2017/0209218 A1 | 7/2017 | Sahay et al. | |

FOREIGN PATENT DOCUMENTS

| | | |
|---|---|---|
| GB | 1108905 A | 4/1968 |
| JP | 2001517475 | 10/2001 |
| JP | 2001520541 A | 10/2001 |
| JP | 2003503123 A | 1/2003 |
| JP | 2004505664 | 2/2004 |
| JP | 2005534460 A | 11/2005 |
| JP | 2008538524 A | 10/2008 |
| JP | 2009500052 A | 1/2009 |
| JP | 2010505527 | 2/2010 |
| JP | 2010528815 A | 8/2010 |
| JP | 2011520513 A | 7/2011 |
| JP | 2011520536 A | 7/2011 |
| JP | 2012196389 | 10/2012 |
| JP | 5383380 B2 | 1/2014 |
| JP | 2016508820 A | 3/2016 |
| WO | WO9204872 A1 | 4/1992 |
| WO | 1998052479 A1 | 11/1998 |
| WO | 9915093 | 4/1999 |
| WO | 9966970 A1 | 12/1999 |
| WO | 200101049 | 1/2001 |
| WO | 0211638 | 2/2002 |
| WO | 0232334 A1 | 4/2002 |
| WO | 2006053308 A2 | 5/2006 |
| WO | WO2009082433 A2 | 7/2009 |
| WO | WO2009082433 A3 | 10/2009 |
| WO | 2009140067 | 11/2009 |
| WO | 2010007954 A1 | 1/2010 |
| WO | 2011/056684 A2 | 5/2011 |
| WO | WO2012006408 A1 | 1/2012 |
| WO | 2015188013 A1 | 12/2015 |

OTHER PUBLICATIONS

International Search Report issued on Mar. 11, 2014 in corresponding International Application No. PCT/US2013/057037.
Supplementary European Search Report mailed Oct. 19, 2016 in related European application 13754251.0 (6 pages).
International Search Report and Written Opinion issued on (Nov. 22, 2011), for PCT/US2013/028935 (11 pages).
International Search Report and Written Opinion issued on (Mar. 11, 2014), for PCT/US2013/057037(12 pages).
S. Smith, "The Scientists and Engineer's Guide to Digital Signal Processing", Jan. 1, 1999, California Technical Publishing, pp. 277-284.
European Search Report issued on (Jan. 1, 2018) for 15803402.5 (10 pages).
Penultimate Office Action mailed Feb. 19, 2020 for Japanese application No. 2018-152432, 14 pages.
Supplementary Partial European Search Report issued on (Dec. 19, 2016), for 13877095.3 (5 pages).
Non-Final Office Action issued in corresponding Japanese application No. JP2014/560134 dated Dec. 20, 2016.
International Search Report and Written Opinion dated Nov. 2, 2015 for International Application No. PCT/US2015/034301(11 pages).
Extended European Search Report for European Patent Application No. 21201198.5 mailed on Apr. 2, 2022, 8 pages.

(56) References Cited

OTHER PUBLICATIONS

Office Action for Japanese Patent Application No. 2015-561321 mailed on Apr. 9, 2018, 5 pages.
Extended European Search Report for Application No. EP20216715.1, dated Jul. 8, 2021, 10 pages.
International Search Report and Written Opinion for International application No. PCT/US2020/055674, mailed on Feb. 9, 2021, 9 pages.

* cited by examiner

CRYOSPRAY CATHETERS

CROSS REFERENCE TO RELATED APPLICATIONS

This application is a continuation-in-part of U.S. patent application Ser. No. 13/784,596 entitled "Cryosurgery System," filed with the U.S. Patent and Trademark Office on Mar. 4, 2013, the specification of which is incorporated herein by reference.

BACKGROUND OF THE INVENTION

1. Field of the Invention

The present invention relates generally to cryospray systems, cryogenic spray ablation and cryosurgery systems, and more particularly to an assortment of improved cryogen delivery catheters for use in cryospray and cryosurgery systems.

2. Description of the Background

The present invention relates to methods and devices for cryospray treatment of organic tissue. Tissue ablation refers to the removal or destruction of tissue, or of tissue functions. Traditionally, invasive and non-invasive surgical procedures are used to perform tissue ablation. These surgical procedures required the cutting and/or destruction of tissue positioned between the exterior of the body and the site where the ablation treatment is conducted, referred to as the treatment site. Cryo ablation is a new alternative in which tissue ablation is conducted by freezing diseased, damaged or otherwise unwanted tissue (collectively referred to herein as "target tissue"). Appropriate target tissue may include, for example, cancerous or precancerous lesions, tumors (malignant or benign), damaged epithelium, fibroses and any other healthy or diseased tissue for which cryo ablation is desired.

Cryo ablation may be performed by using a system that sprays low pressure cryogen on the target tissue. Such systems are often referred to as cryospray systems, cryosurgery spray systems, cryosurgery systems, cryogen spray ablation systems or simply cryospray ablation systems. As used typically, cryogen refers to any fluid (e.g., gas, liquefied gas or other fluid known to one of ordinary skill in the art) that has a sufficiently low boiling point to allow for therapeutically effective cryotherapy and is otherwise suitable for cryogenic surgical procedures. For example, acceptable fluids may have a boiling point below approximately negative (−) 150° C. The cryogen may be liquefied nitrogen, as it is readily available. Other fluids such as argon and air may also be used. Additionally, liquid helium, liquid oxygen, liquid nitrous oxide and other cryogens can also be used.

During operation of a cryosurgery system, a clinician, physician, surgeon, technician, or other operator (collectively referred to as "operator" herein), sprays cryogen on the target tissue via a delivery catheter. The spray of cryogen causes the target tissue to freeze or "cyrofrost." The physician may target the cryospray visually utilizing endoscopy, bronchoscopy, pleuroscopy, or other video assisted device or scope. The temperature range can be from negative 0° C. to (−)195° C. This latter temperature in particular is the case of liquid nitrogen at low pressure.

SUMMARY OF THE INVENTION

The invention includes a catheter apparatus that allows for evenly distributed cryospray treatment of a tissue cavity within the human body. The method involves the use of an endoscope or bronchoscope (either which sometimes referred to hereinafter as "scope") for the navigation and visualization of the target tissue, the use of a directed spray catheter with a straight or a radial spray head to treat such target tissue after positioning such catheter in a center or near center position via markers on the apparatus. The method and device of the invention targets the tissue circumferentially (in the case of a radial spray head) with a direct cryogen contacting spray onto such tissue. In use, the catheter is inserted into the working channel of a scope, which in turn is utilized to locate the target tissue. The catheter is connected to a cryospray console that houses and delivers cryogen fluid to the catheter. Since most bronchoscopes have a working channel that is offset from the center, the invention also allows for centering of the catheter as it exits an off-center working channel as it is targeting tissue. As a result, one embodiment of the invention centers the catheter in relation to the tissue cavity area for even dose delivery in the lumen.

According to one aspect of the present invention, there is provided an advanced cryosurgery system having improved cryogen flow and flow control, an integrated suction pump, a pressure sensor and an improved delivery catheter.

Embodiments of the present invention are directed to a cryospray system having a cryogen delivery apparatus. In accordance with embodiments of the present invention, the cryospray system may further include a cryogen source configured to provide the cryogen to the cryogen delivery apparatus, a regulation apparatus fluidically coupled to the cryogen source and to the cryogen delivery apparatus, and a controller communicatively coupled to the regulation apparatus configured to control the release of cryogen into the cryogen delivery apparatus. Exemplary cryosurgery systems in which the present invention may be implemented include, but are not limited to, those systems described in commonly owned U.S. Pat. Nos. 7,255,693, 7,025,762, 6,383,181, and 6,027,499 and U.S. patent application Ser. No. 11/956,890, U.S. patent application Ser. No. 12/022,013, U.S. patent application Ser. No. 13/411,395, and U.S. patent application Ser. No. 13/784,596, each of which are incorporated herein in their entirety. Embodiments of the present invention are described below in connection with one embodiment of such exemplary cryosurgery system shown in FIG. 1.

The system of the present invention is a cryosurgical tool that applies a medical-grade liquid nitrogen spray (or other cryogen) to the treatment area via a small, low pressure, open tipped catheter.

The prior art includes cryospray ablation catheters with straight spray patterns that are directed at tissue in one modality. The present invention provides a cryospray physician with additional maneuverability to ensure that the proper target is sprayed. The cryospray catheter is constructed with material and design features that allow for full maneuverability during spray targeting as well as retention of function at the cryogenic temperatures.

The present invention includes a catheter having a set of features that provide the flexibility and targeting to provide a clear way of targeting the tissue, without hindering scope functionality. According to further embodiments, the catheter has features that allow for tissue targeting of segments or tissue areas using straight spray and/or radial spray patterns. According to yet further embodiments, the catheters of the invention may include structures for centering the catheter as it exits a working channel of the scope, as well as structures for permitting catheter rotation during tissue targeting. Accordingly, the catheters of the invention provide targeting functionality that exceeds and extends prior art targeting that was limited by the capabilities of the scope.

The invention is a catheter that contains the necessary features to provide an even contiguous treatment and depth of thermal injury of the target tissue. This is achieved via a combination of a fenestrated hole pattern for cryospray, the shape of the catheter tip to create a centering orientation with respect to the actual scope utilized to guide the cryospray catheter, and/or the additional centering apparatus that helps center the catheter with respect to the treatment tissue cavity or lumen, which can be of varied size. These features provide the optimal dose of cryospray in a set flow rate and fast delivery time to optimize its practicality.

The preferred catheter construction includes materials selected to maximize heat conductivity that allows for cryo cooling of the catheter fluid path ahead of the dual phase flow. This is achieved with a balance of metal tubing and polymeric layering with metal braiding/coiling. It can also include the selection of diameters along its length to help deliver such right amount of cryogen flow rate. One embodiment has a centering feature that allows for rotation of the catheter within the scope working channel. This feature provides an additional degree of freedom during the navigation and targeting of the scope with catheter combination to help provide more accuracy in targeting the lumen center prior to treatment.

The catheter may contain a thermocouple wire at the distal tip of the catheter near the radial spray head to help provide information to the console connected to the catheter. This information is related to the temperature either within or on the catheter shaft and may be used to provide information or feedback control on the dose provided by the cryospray ablation system.

According to preferred embodiments of the invention, the improved catheters disclosed herein may include one or more of the following features and advantages:
- repeatable spray patterning of the treatment cavity.
- centering of the catheter with respect to the scope.
- centering of the catheter spray head with respect to the treatment cavity.
- uniform circumferential spray of cryo media delivering a controlled contiguous hypothermic dose to the lumen.
- repeatable set dose with reference to time of spray, dwell time and treatment distance.
- fast time to freeze based on the combination of material construction, catheter working length proximal to distal shaft length ratio, and diameter.
- absence of material contact in the direct spray area, which prevents the adhesion to tissue
- temperature feedback loop to console system for spray time. The temperature reported is the temperature at the tip of the catheter outer layer which is an indication of the presence and temperature slope of the cryogen traveling to that point. In addition, the temperature of the output spray fluid may also be reported by locating the thermocouple junction within the spray path or at one of the radial spray hole outputs.

According to one embodiment of the invention, a cryospray catheter may include:
- a proximal metal interface "bayonet" that can be connected to the console;
- an ergonomic plastic cover to interface with console along with the bayonet;
- an insulating sheath distributed over the proximal portion of the catheter assembly which resides outside the working channel of the scope;
- a large diameter proximal tube (ranging from 0.060" to 0.120" I.D. with preferred I.D. of 0.104");
- an outer covering in the form of a polymeric layer to cover a portion or the entire length of the proximal tube to provide a fluid tight lumen; and
- a small diameter distal tube (0.048" to 0.070" I.D. with 0.061" I.D. preferred) of polyimide and braid construction of 30 to 50 inches long, 33 inches preferred.

According to an embodiment of the invention, the proximal tube may be made of metal hypotube, with the preferred embodiment constructed from stainless steel hypotube, with a length of up to 85" working length, with varying laser cut stiffness profile, providing stiffness properties in the hypotube ranging from a stiffer proximal to a more flexible distal, preventing any abrupt transition and avoiding kinking. The hypotube may contain solid regions at each end for joining.

According to an alternative embodiment, the proximal tube may be made of metal ribbon (or flat wire) formed into a coil of the desired diameter.

According to alternative embodiments, the small diameter distal tube can similarly be constructed using metal hypotube, or flat or round wire formed into a coil instead of the polyimide and braid construction described above.

According to one embodiment of the invention, the small distal tube may terminate in a single end hole (configured for a straight spray). According to alternative embodiments, the small distal tube may be provided with a plurality of holes in its side arranged in a radial hole pattern. Fenestrations are distributed at the distal end of the catheter in a radial configuration arranged around the circumference of the tube. The radial configuration may be varied according to different tissue treatment and/or targeting conditions. Specifically, the number of holes per cm of circumference can be varied, as can the number rows per centimeter per length of distal tip, the number of sections with holes, the diameter of each hole (fixed or variable), and the shape of the holes (i.e., circular, rectangular, triangle, pentagon, etc.), all with the purpose of treating a specific area with a specific cryogenic effect. Additionally, the quantity and pattern of holes in the hole array may vary depending on pressure pre-set on console and desired treatment dose to the tissue.

According to a radial spray embodiment, further embodiments of the invention may include one or more markings or bands to signify treatment area, preferably one at each end of the radial spray pattern. These bands may be created by pad printing or laser marking or other known techniques.

According to a further embodiment of the invention, the catheter may contain a temperature sensing component at the distal end next to the radial spray pattern. According to preferred embodiments of the invention, the distal portion of the small distal tube may be provided with markings to provide a visual indication of the position and orientation of the tip.

According to further alternative embodiments of the invention, the catheter may include a centering feature for optimal positioning in the treatment area. In a preferred embodiment, the centering feature comprises of pre-shaped S-curve. The S-curve can be made more or less pronounced to further offset the catheter from the centerline of the scope, if desired. This offset can further enhance the extra degree of motion provided by rotating the polymeric or metallic junction of the catheter within the working channel.

According to embodiments which include a centering feature, further embodiments may include an axial marking printed along the shaft to signify the orientation of such centering feature.

Still yet further embodiments may include an occluded, rounded device tip, which serves to both force the spray pattern out the fenestrations while also providing an atraumatic tip to prevent tissue injury Further embodiments of the invention may include a polymeric or metallic nozzle junction to funnel flow as it transitions from a large diameter I.D. to a smaller diameter I.D. According to these embodiments, the polymeric or metallic junction may be located at the junction where the large inner diameter shaft meets the smaller inner diameter shaft. According to further embodiments, the polymeric or metallic nozzle junction may contain a width extension with a preferred geometry of wings for aiding the user to torque the distal shaft as a way to help navigate the scope and catheter to an optimal position for cryospray treatment.

According to alternative embodiments of the invention, the catheter shaft may be straight or substantially straight and contain no centering feature.

According to further embodiments of the invention, the catheter may be provided with a self-centering mechanism constructed of a self-expanding heat formed FEP, PTFE, spring steel or Pebax structure, a spring that travels along the inner length of the self-expanding polymeric spherical structure (FEP, PTFE or Pebax), and a round stainless steel tip that forms an atraumatic tip to the catheter, but also is the area for bonding the FEP or Pebax structure to the inner spring. This self-expanding structure can result in a spherical or oval shape with multiple extensions ranging from 1 to 10 filaments that make up the structure. The self-expansion can allow the catheter to keep the surface of the catheter away from the tissue for allowing the spray to be more uniform and/or to center the catheter spray head around the lumen to help provide maximum coverage to the targeted quadrant or quadrants. Target quadrants are defined as areas of the lumen that can be treated between a range of treatment around a circumference. The area of treatment varies between spraying an angular coverage between 0 and 30 degrees to 0 and 90 degrees, 0 and 180 degrees and 0 and 360 degrees as well as anything in between.

A self-centering apparatus may comprise of a chromium cobalt/stainless steel mesh as its self-adjusting structure.

According to an alternative self-centering embodiment of the invention, the self-centering mechanism is not self-expanding, but instead it may be expanded by the user upon engaging a proximal mechanism (to the user) such as a wire or spring trigger. According to this embodiment, the catheter is inserted into the scope working channel and exits the scope at the distal end. Once the user sets it over the target treatment tissue, the user engages the centering mechanism which in turn expands to the lumen size.

According to yet another embodiment of the invention, a cryospray catheter may include an all-polymeric shaft construction for the catheter length, with a proximal end of a varying inner diameters for a length up to the working channel entrance, and a distal section of same or smaller diameter that can be adjusted to fit the working channel of the scope to target a specific flow and to target a specific volume of cryogen within a specific time of spray. This embodiment may be provided without or without a centering feature.

According to one embodiment, the ability of the catheter to deliver cooling can be influenced by the thermal conductivity of the catheter materials and/or construction. Thermally conductive materials can be incorporated into the design to improve the rate of cooling of the catheter materials to help maintain the liquid phase of the flow through such catheter. Certain metals and/or ceramics and/or nanoparticles and structures can be incorporated into the polymeric material to increase the heat capacity of the compound (s) from which the catheter is made. One example is the addition of boron nitride into the catheter material. Similarly, support structures in the catheter tube such as braid, coils, and/or longitudinal support members can be incorporated and/or maximized to improve the rate of cooling of the catheter.

Additionally, the catheter may also be of various lengths. Another embodiment may have the catheter be the same diameter from proximal to distal.

Other embodiments are possible for radial spray including a hollow cone spray.

The catheter may also be fully constructed of metal hypotube laser cut profile for flexibility and wrapped by a polymeric outer jacket as a way to create a fluid tight seal between the ID and OD of the catheter.

The catheter may change inner diameters along its length more than once to control size and/or as a way to control flow and volume delivery.

According to a further embodiment, the catheter of the invention may be fitted with a cyclone tube to help funnel cryogen liquid into the lumen of a multi-lumen shaft section that is meant for cryospray. The funneling helps concentrate the cooling power of the fluid output by concentrating the liquid output to the cryogen ablation site. According to a preferred embodiment, the cyclone tube may be manufactured from quartz or pyrex. According to an alternative embodiment, the cyclone tube may be cast from a thermoset or metal. The cyclone tube may be located anywhere along the length of the catheter, but according to a preferred embodiment, it may be located at the junction between the proximal and the distal portions of the catheter.

According to yet another embodiment of the invention, an egress tube may be configured to fit over the length of a bronchoscope or endoscope. The interior of the egress tube may be configured with spacing elements to create space between the interior surface of the egress tube and the exterior surface of the scope to allow for passive/active venting of gas in cryospray therapy. The egress scope preferably encapsulates the scope, providing added insulation. In addition, the egress tube serves as an aide to center the working channel of the scope. According to alternative embodiments, the egress tube may have a dedicated lumen for pressure sensing.

BRIEF DESCRIPTION OF THE DRAWINGS

FIG. 1 is a perspective view of a cryosurgery system according to an embodiment of the invention;

FIG. 2 is a perspective view of a cryosurgery system according to an embodiment of the invention;

FIG. 3 is a perspective view of a cryosurgery system according to another embodiment of the invention;

FIG. 4 is an isometric view of a radial spray catheter according to an embodiment of the invention, with an S-curve centering feature attached.

FIG. 5 is a side view of the distal end of an alternate embodiment including a radial spray pattern with marking bands and self-centering mechanism in the form of a self-expanding sphere frame.

FIG. 6 is a side view of the steel tube proximal construction of a catheter according to the invention with a laser cut pattern that varies to adjust tube flexibility.

FIG. 7 is a side view of the S-shape curve aligned to the centerline of the scope (radial spray and atraumatic tip not shown).

FIG. 8 is an illustration of a polymeric junction to funnel flow and wings for torqueing the distal shaft to help navigate the scope and catheter to an optimal position for cryospray.

DETAILED DESCRIPTION

Figure 1:
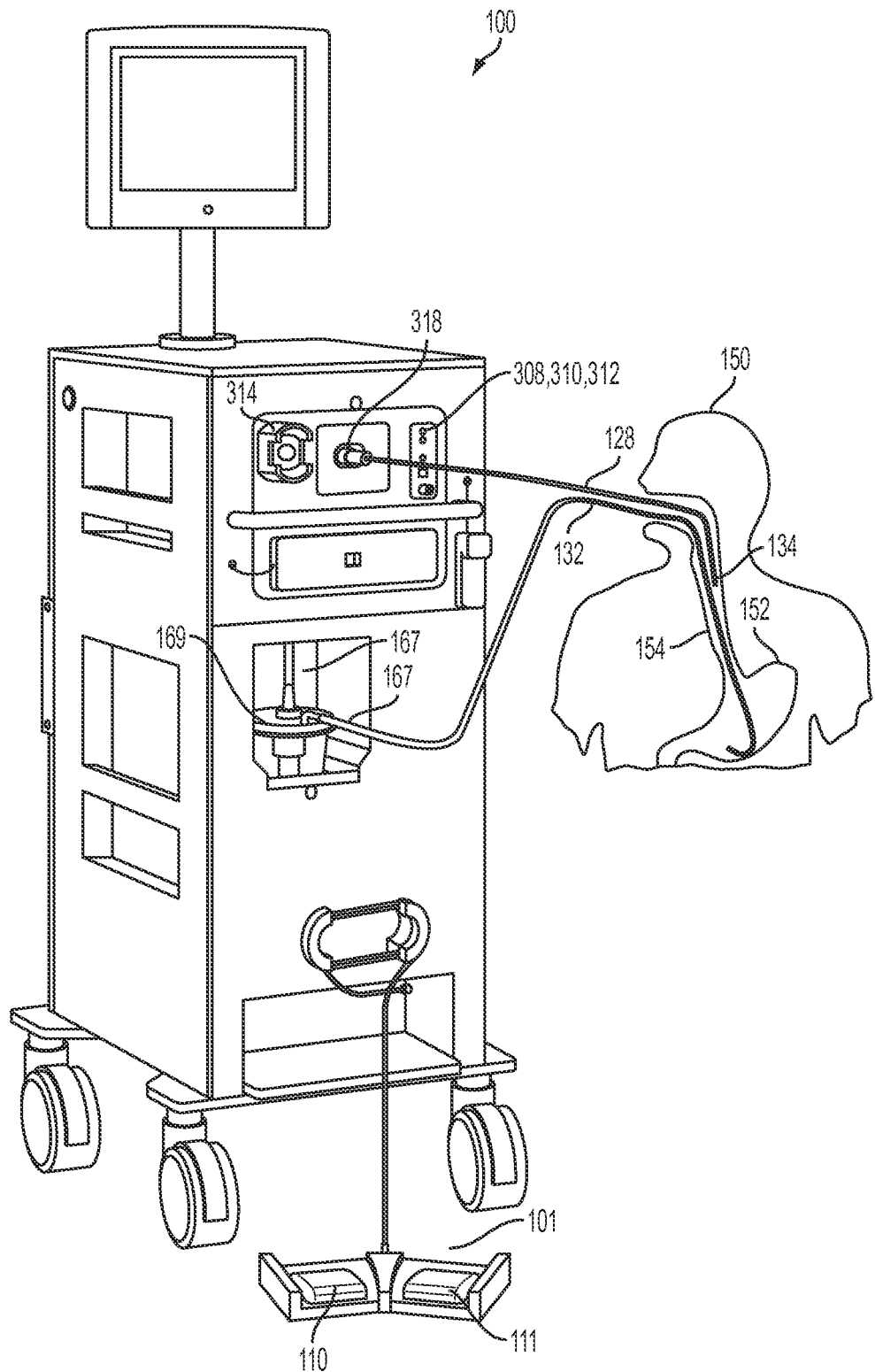
Figure 2:
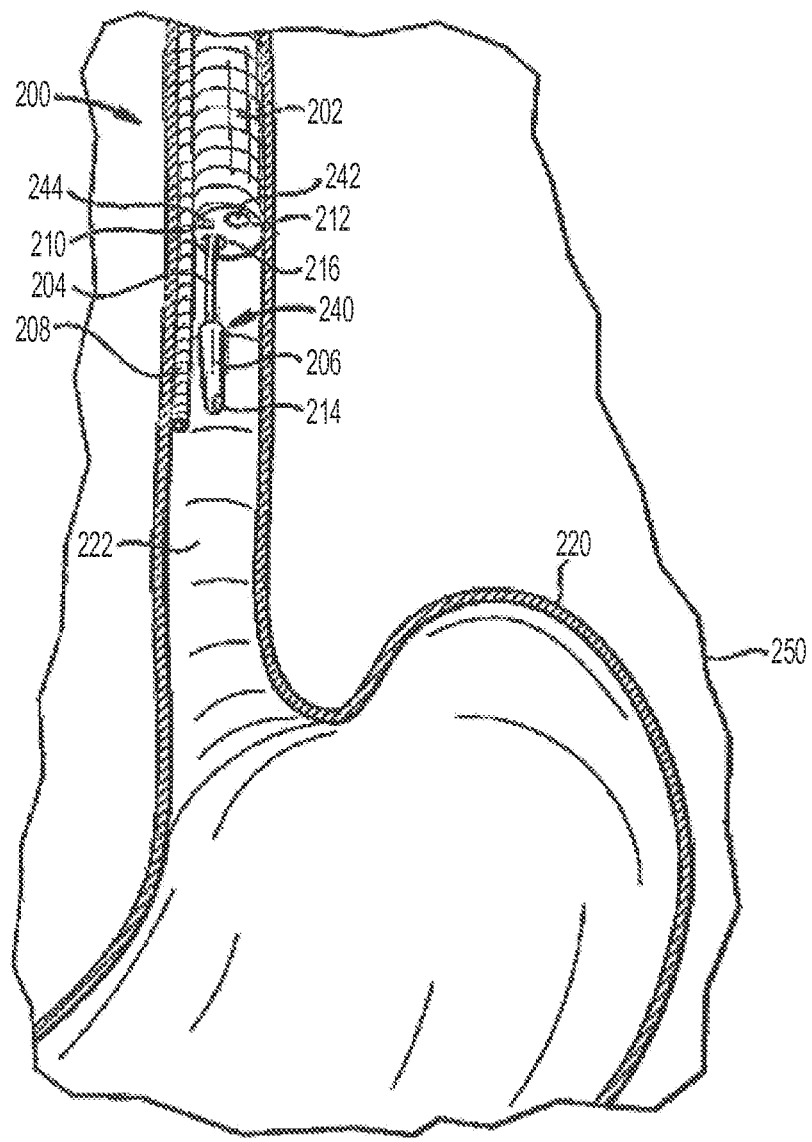
Figure 3:
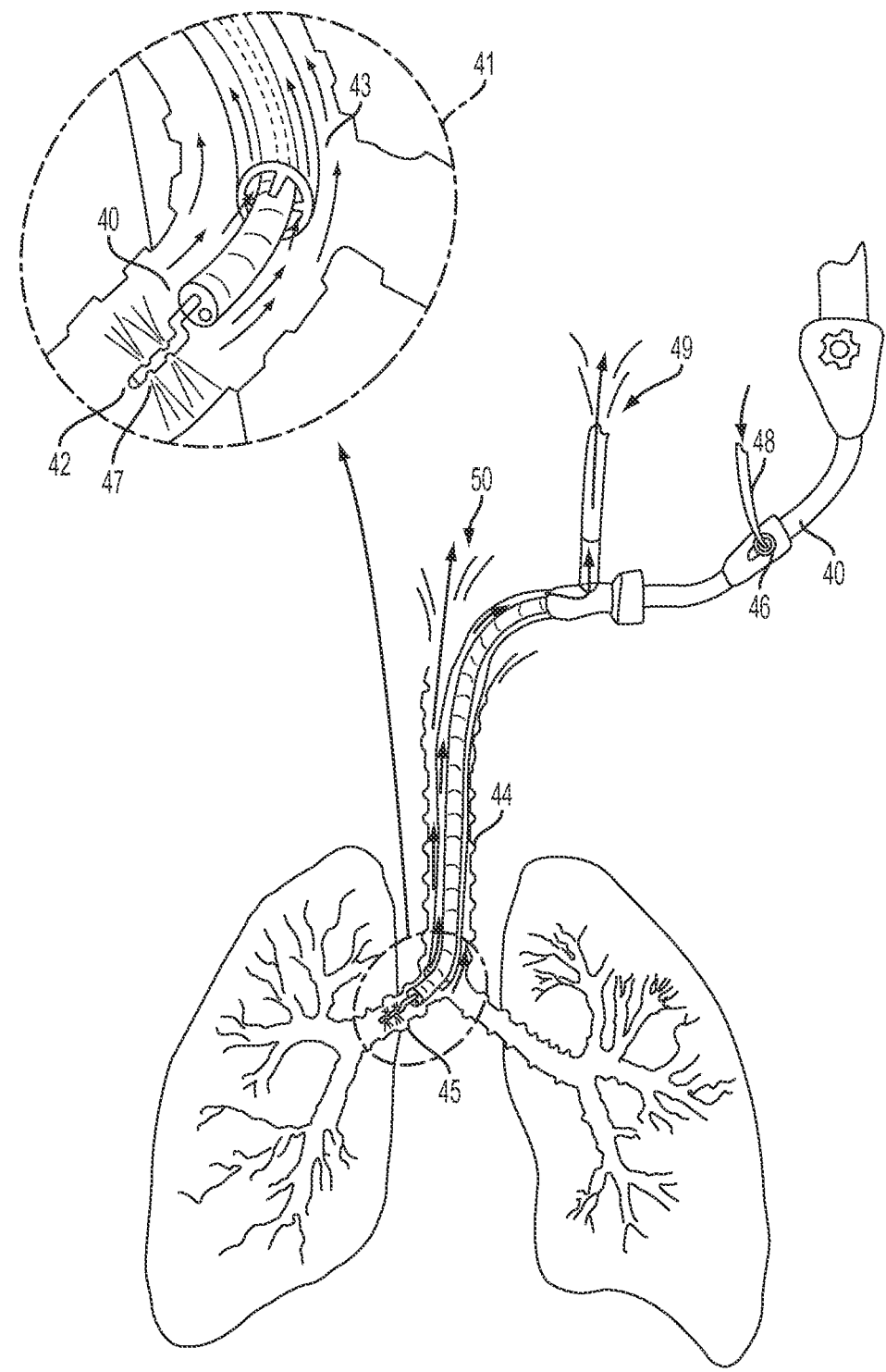

A simplified perspective view of an exemplary cryosurgery system in which embodiments of the present invention may be implemented is illustrated in FIGS. 1, 2 and 3. Cryosurgery system 100 comprises a pressurized cryogen storage tank 126 to store cryogen under pressure. In the following description, the cryogen stored in tank 126 is liquid nitrogen although cryogen may be other materials as described in detail below. The pressure for the liquefied gas in the tank may range from 5 psi to 90 psi. According to a more preferred embodiment, pressuring in the tank during storage is 40 psi or less, and pressure in the tank during operation is 35 psi or less. According to a more preferred embodiment, pressure in the tank during storage is 35 psi or less and pressuring during operation is 25 psi or less. According to a most preferred embodiment, pressure during operation at normal nitrogen flow is 22±2 psi, and pressure during operation at low nitrogen flow is 14±2 psi. When the pressure in the tank during operation is set to 22 psi, the flow rate/cooling capacity of the nitrogen is 25 W. When the pressure in the tank during operation is set to 14 psi, the flow rate/cooling capacity of the nitrogen is 12.5 W. In an alternate embodiment, the cryogen pressure may be controlled all the way to 45 PSI and to deliver through smaller lumen catheters and additional feature sets. In such alternate embodiments the pressure in the tank during storage may be 55 psi or less. In the context of the output pressure of cryospray from the distal end of the catheter, the term low pressure means 2 psi to 20 psi.

In the embodiment illustrated in FIG. 1, a conventional therapeutic endoscope 134 is used to deliver the nitrogen gas to target tissue within the patient. Endoscope 134 may be of any size, although a smaller diagnostic endoscope is preferably used from the standpoint of patient comfort. In certain embodiments, a specially designed endoscope having a camera integrated therein may also be used. As is known, an image received at the lens on the distal end of the camera integrated into endoscope 134 may be transferred via fiber optics to a monitoring camera which sends video signals via a cable to the a conventional monitor or microscope, where the procedure can be visualized. By virtue of this visualization, the surgeon is able to perform the cryosurgery at treatment site 154.

As the liquid nitrogen travels from tank 126 to the proximal end of cryogen delivery catheter 128, the liquid is warmed and starts to boil, resulting in cool gas emerging from the distal end or tip of catheter 128. The amount of boiling in catheter 128 depends on the mass and thermal capacity of catheter 128. Since catheter 128 is of small diameter and mass, the amount of boiling is not great. (The catheter would preferably be of size seven French.) When the liquid nitrogen undergoes phase change from liquid to gaseous nitrogen, additional pressure is created throughout the length of catheter 128. This is especially true at the solenoid/catheter junction, where the diameter of the supply tube to the lumen of catheter 128 decreases from approximately 0.25 inches to approximately 0.070 inches, respectively. But the catheter range diameter of its lumen may be between 0.030 to 0.125 inches. In an alternate embodiment the gas boiling inside the catheter may be reduced even greater by the use of insulating materials such as PTFE, FEP, Pebax and others to help reduce its temperature coefficient. The addition of PTFE is especially desirable if done in the inner lumen because its lower coefficient of friction aids in laminar flow of the fluid and thus reducing turbulence and entropy. This reduces gas expansion and allows for good fluid velocity.

When the liquid nitrogen reaches the distal end of catheter 128 it is sprayed out of cryogen delivery catheter 128 onto the target tissue. It should be appreciated that certain embodiments the cryosurgery system may be able to sufficiently freeze the target tissue without actual liquid nitrogen being sprayed from catheter 128. In particular, a spray of liquid may not be needed if cold nitrogen gas is capable of freezing the target tissue.

Freezing of the target tissue is visually apparent to the physician by the acquisition of a white color, referred to as cryofrost, by the target tissue. The white color, resulting from surface frost, indicates the onset of mucosal or other tissue freezing sufficient to initiate destruction of the diseased or abnormal tissue. The operator may use the system timer to freeze for a specified duration once initial cryofrost is achieved in order to control the depth of injury. In one embodiment, the composition of catheter 128 or the degree of insulating capacity thereof will be selected so as to allow the freezing of the tissue to be slow enough to allow the physician to observe the degree of freezing and to stop the spray as soon as the surface achieves the desired whiteness of color. The operator may monitor the target tissue to determine when cryofrost has occurred via the camera integrated into endoscope 134. The operator manipulates cryogen catheter 128 to freeze the target tissue. Once the operation is complete, cryodecompression tube 132, catheter 128, and endoscope 134 are withdrawn.

Catheter length may be anywhere from 10 inches to 100 inches. Inside diameter of the catheter may be anywhere from 0.8 mm to 5 mm, preferably from 1 mm to 4 mm. The tank size may be anywhere from 5 L to 100 L; its diameter may range from 4 inches to 36 inches. The vent orifice of the manifold may be 0.01 inches to 0.1 inches.

FIG. 2 is a perspective view of a portion of a cryosurgery system 200 having a cryogen delivery apparatus 240. Cryosurgery system 200 comprises an endoscope 202 having lumens 210, 212 and 216 therein. As shown, endoscope may be positioned in the esophagus 222 of patient 250. Lumen 212, disposed in endoscope 202, is configured to receive an endoscope camera 242. Lumen 210 may be configured to receive a light 244 for illumination of the treatment site. Lumen 216 of scope 202 may be configured to receive cryogen delivery apparatus 240. Cryogen delivery apparatus 240 comprises a retroflex-capable cryogen delivery catheter 204, catheter tip 206, and one or more holes 214. After insertion of the cryogen delivery apparatus into the patient, cryogen is provided to cryogen delivery catheter 204 from a cryogen source. Tip 206 causes the cryogen to be sprayed on the target tissue via hole 214. A dual lumen (for both passive and active venting) cryodecompression tube 208 may be provided to evacuate the treatment area of undesirable gases, particles, fluids etc.

Alternatively, the controlled pressure and pulsing, coupled with careful control of catheter diameter, length and material composition, helps further deliver controlled flow of volume over time that is consistent with the cryogenic property of the fluid being delivered. Dual phase fluid flow is achieved out of the catheter distal tip and maintained constantly via the equilibrium that the system achieves after pre-cool and after the catheter achieves a cold temperature. The range of dual phase fluid cryogen delivery out of a cryogen catheter with this system can range from 5 LPM to 50 LPM (once it all expands into gas).

FIG. 3 is a perspective view of a portion of a cryosurgery system 41 having a cryogen delivery apparatus 42. Cryosurgery system 41 comprises a bronchoscope 40 and a catheter tip 42 exiting its working channel. As shown, bronchoscope 40 may be positioned in the trachea 44, or bronchi—such as the principle bronchi 45 of patient. The catheter 48 is placed in the working channel lumen 46 of the scope 40 and exits the working channel at the distal tip of the scope. Cryogen delivery apparatus 42 comprises a radial spray cryogen delivery catheter at distal end 42, and one or more holes 47. After insertion of the cryogen delivery apparatus into the patient, cryogen is provided to cryogen delivery catheter 48 from a cryogen source. Catheter distal end with one or more holes 42 causes the cryogen to be sprayed on the target tissue via hole(s). A gas egress tube 43 that surrounds the scope may be utilized to provide additional means to evacuate the treatment area of the cryogenic gas out of the patient 49. Passive lumen egress 50 is also present via the management of the airway to ensure proper venting during the procedure.

Catheter

The catheter is designed to transport liquid nitrogen (or other cryogen) from the console to the patient treatment site. According to one embodiment, the catheter may contain (1) a bayonet and hub for attachment to the console at its proximal end, (2) a layered polyimide and stainless steel braided shaft to minimize kinking and breaking, (3) insulation to protect the user from cold, (4) a strain relief to help prevent kinking when torqued by users and (5) an atraumatic tip at its distal end to prevent damage to tissue. The laminated construction and braided material provides additional strength and flexibility, allowing the physician to retroflex the catheter during a treatment procedure, if needed. The catheter pouch may contain an RFID tag that the user scans prior to use to prevent reuse and track disposable information. The catheter pouch may also contain an introducer that provides reinforcement for the catheter and helps prevent kinking during use and when placing the catheter into the scope. An alternative construction locates the RFID tag on the connector area adjacent to the bayonet.

According to a preferred embodiment, the delivery catheter may be constructed of three layers of flexible polyimide, surrounded by a stainless steel braid, which is in turn coated with an outer layer of Pebax. It was discovered that that extrusion of Pebax over the stainless steel braid allows the Pebax to wick through the pitch of the steel braid, helping to prevent kinking, breaking, or delamination during retroflex of the catheter. The Pebax also provides a desirable balance between hardness—important for smooth sliding of the catheter and general toughness, and softness, which is important for some degree of tackiness which allows the user to feel the movement of the catheter in the scope. The pitch of the stainless steel braid is configured to be fine enough to afford the required strength, not thick enough to allow the Pebax to wick through. The distal end of the catheter is provided with an atraumatic tip comprised only of Pebax, in the shape of a bullnose. This novel construction allows for retroflex of the catheter without kinking, breaking, or delamination of the catheter. For the purposes of this invention, retroflex is used to refer to the ability of a catheter to bend or turn approximately 180° about a radius of curvature of 1 inch or less. This is useful so that when the catheter is introduced into, for example, the stomach via the esophagus, the catheter can be turned approximately 180° in order to treat the roof of the stomach.

Figure 4:
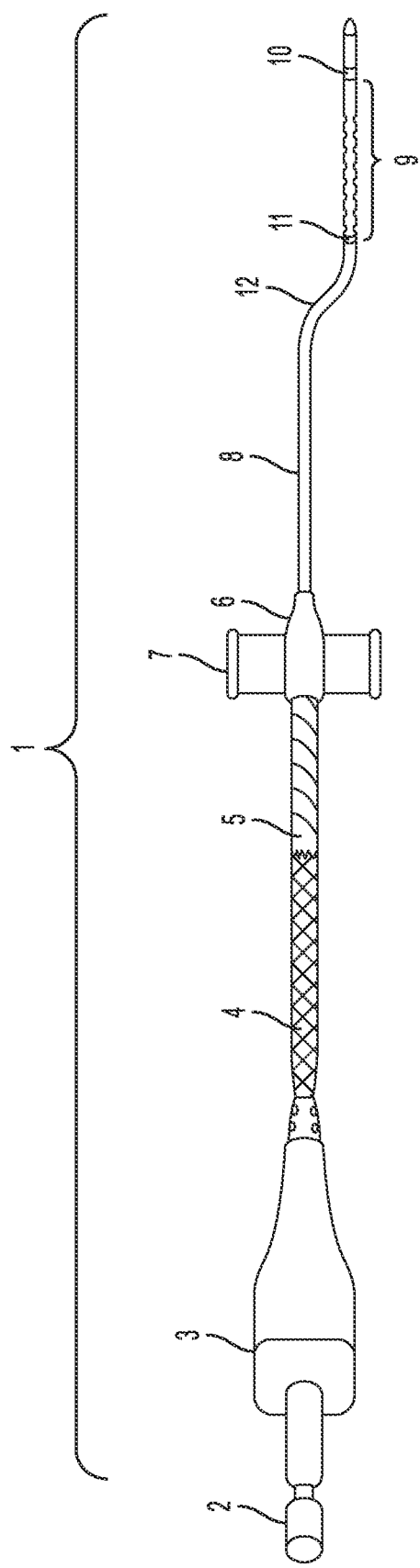

FIG. 4 shows the preferred embodiment catheter construction of the cryospray catheter 1 according to the invention. It includes a bayonet connection 2, catheter connection housing 3, insulation 4, laser cut hypotube with FEP or Pebax heatshrink wrap 5, nozzle connection of diminishing inner diameter 6 with wings for torqueing 7, multilayer polymeric shaft 8, radial spray pattern 9, spray pattern indicator marking bands at tip 10, spray pattern indicator marking band at other end of hole pattern 11, S-curve shaped shaft area 12.

By adding very thin layers of metal to the catheter shaft or increasing the heat transfer coefficient in the shaft by adding a braided metal for example, the catheter may be constructed to provide optimal cryo delivery to the tip of the device in a very short cycle time.

Figure 5:
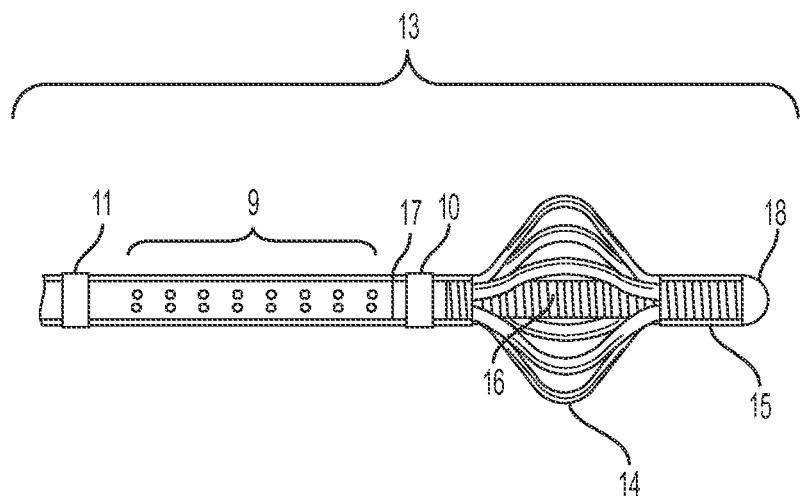

FIG. 5 shows a close-up of a catheter tip 13 with alternate construction utilizing a self-expanding spherical polymeric frame 14. This frame is preferably made out of a Pebax extrusion and laser cut into multiple slits along its length. When the end shape is compressed, it forms the spherical frame shape 14 on the illustration. The frame is held in place by center shaft 15 containing a spring 16 which keeps the frame in compression until it is inserted into a small lumen which collapses the spherical frame 14 and stretch the center shaft spring 16. FIG. 5 also shows the radial spray pattern 9 bracketed by the markings that delineate the beginning and end of the radial spray. FIG. 5 also shows a radial spray hole pattern that extends for 1 mm distance longitudinally and contains 8 rows of holes along the circumference to target a lumen at 360 degrees cryo spray coverage. The fenestrated hole pattern can vary with embodiments meant to target less or more longitudinal distance. The hole pattern can also be cut to target a quadrant or quadrants along a lumen ranging from 0 degrees to 360 depending on desired spray coverage. The size of the holes on the embodiment on the illustration are 0.015 inches. However, the hole sizes can vary from 0.004 inches to 0.030 inches in diameter. Additionally, the holes can be any shape, e.g., round, square, diamond, oval, rectangular, star-shaped, etc.

Continuing on FIG. 5, the spray is blocked by the center shaft and spring assembly at 17. This ensures that the cryogen exits the fenestrated holes 9 and not the end of the shaft. The opposite end of the sphere 14 contains a machined piece 18 that is utilized to secure the spring 16 and form an atraumatic tip area at the end of the catheter.

Figure 6:
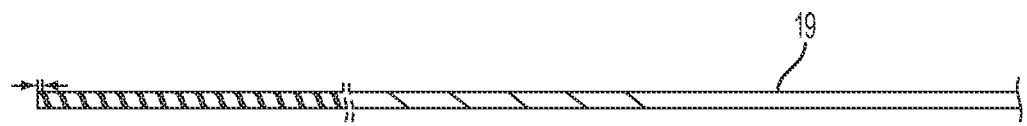

FIG. 6 shows a typical hypotube 19 used for the construction of the proximal end of the catheter shaft 5. It typically has a length of 50 inches but can vary from 24 to 96 inches in length. The internal diameter of the tube 19 is usually 0.104 inches but can vary between 0.045 to 0.150 inches. In the preferred embodiment, the hypotube 19 may be laser cut as a spiral, but other variable cuts can be present. The cuts provide flexibility to the metal tube.

Figure 7:
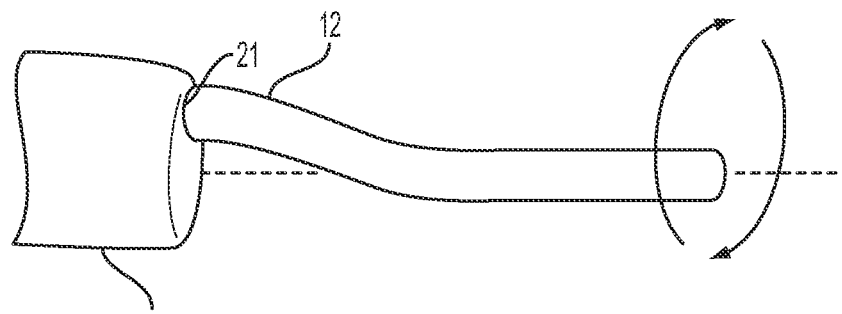

FIG. 7 shows the S-curve 12 seen on FIG. 4 when used with the scope for centering the spray with respect to the diameter of the scope 20 and the working channel exit 21, which is off center on the scope. According to this embodiment, the catheter can be rotated along the axis of the working channel 21, providing a level of alignment along the lumen that allows for centering of the spray pattern by the user as the tissue is targeted for cryo spray ablation.

Figure 8:
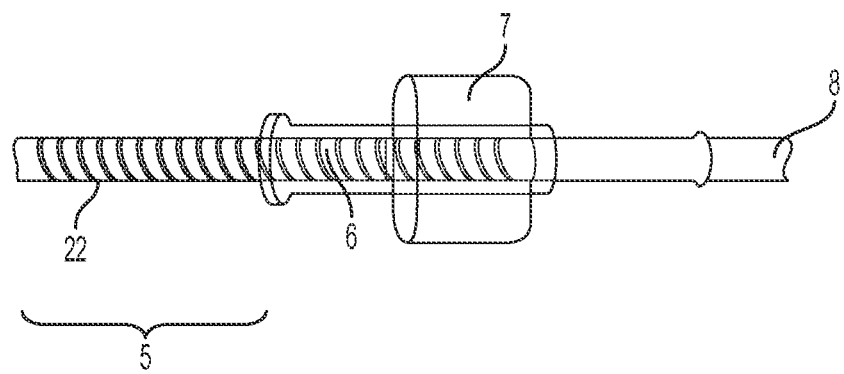

FIG. 8 shows a catheter construction in which proximal metal tube with outer polymeric liner is constructed out of a pre wound wire coil 22. This coil provides the cold conduction as the cryo spray is applied ahead of the dual phase flow to help establish a low temperature gradient between the materials and the cryogenic fluid in the catheter.

The coil shown in FIG. 8 is then mated to a polymeric junction 6 that serves various functions, such as strain relief, fluid transition from a large diameter to a small diameter, and it provides a torque point for the distal catheter in catheters with the S-curve as the centering feature. To aid in the torqueing, wings 7 are provided on the junction.

Figure 9:
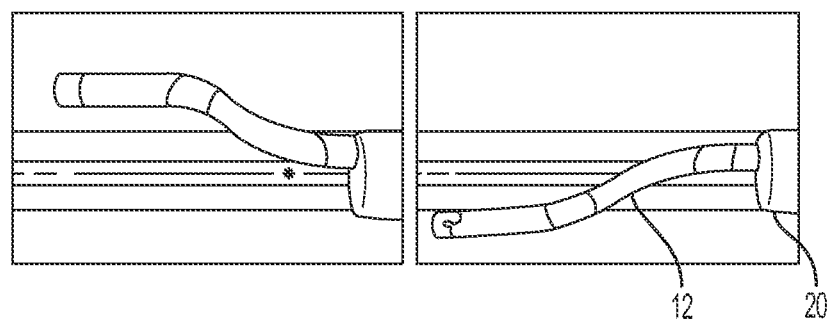
FIG. 9 shows an exaggerated S-curve for added directional control within the anatomy.

FIG. 9 shows an S-curve feature 12 on the catheter that is pronounced or exaggerated beyond the center of the scope 20. The pronounced or exaggerated S-curve provides improved positioning in the larger lumen and smaller lumen selection and navigation more navigation in larger lumen areas of the body. By torqueing the exaggerated curve 12, along with the scope 20 manipulation and flexing, the navigation of the scope 20 may be enhanced.

Figure 10:
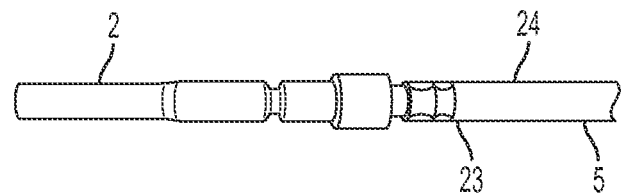
FIG. 10 shows a bayonet connector, according to an embodiment of the invention, welded to the hypotube and such hypotube wrapped in heatshrink.

FIG. 10 shows the junction 23 of the bayonet console connector 2 to the hypotube 19 or coil 22 (not shown in FIG. 10). The hypotube 19 may be welded to the bayonet 2 to create an all-around seal around the metal junction 23. An FEP heatshrink 24 may be applied to the entire length of the hypotube 19 or coil 22. The heatshrink 24 can also be Pebax or PET. FEP heatshrink is preferred for cryogenic applications.

Figure 11:
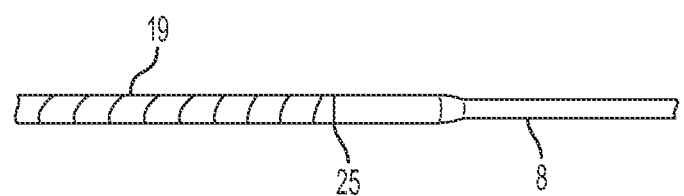
FIG. 11 shows a side view of one embodiment of the junction of a large I.D. hypotube to a small I.D. polymeric shaft

FIG. 11 is shows a transition 25 of a large diameter hypotube shaft 19 to a small diameter polymeric shaft 8. The transition is so that a smaller diameter can be inserted into the working channel of a scope. In addition, the transition from large diameter to small diameter acts as a mixing point for the dual phase flow gas and liquid to interact along the catheter path and allow for the gas to once again attain the velocity of the liquid as they travel down the pipe. This transition is referred to as a "nozzling" transition. This transition can occur between two hypotubes, two polymeric shafts or between a coil and hypotube or coil and polymeric shaft.

Figure 12:
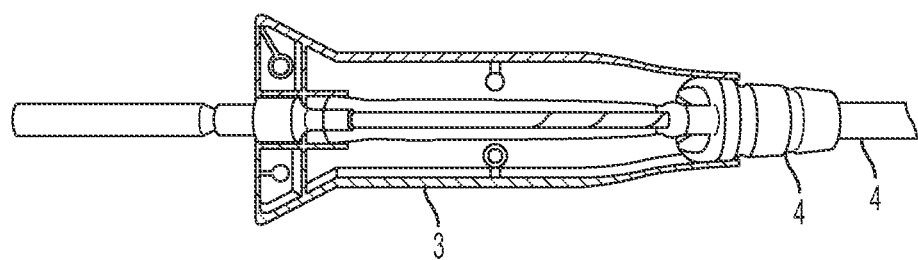
FIG. 12 shows the insulator and connector housing area with the bayonet, according to one embodiment of the invention.

FIG. 12 shows the insulator 4 and the connector housing 3 added to the catheter assembly 1.

Figure 13:
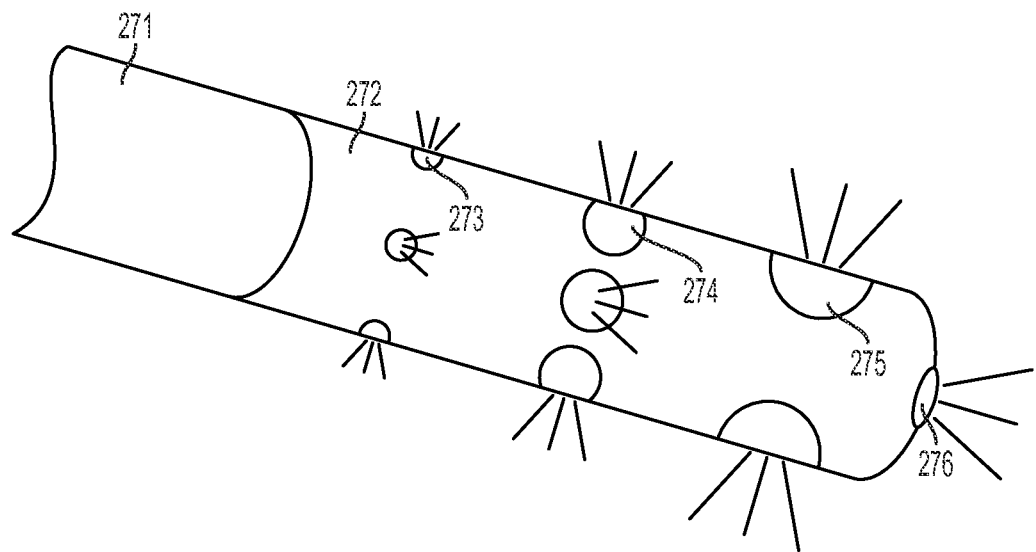
FIG. 13 shows an embodiment of the invention according to which a catheter radial spray pattern is supplemented by a straight spray

FIG. 13 shows a design in which the catheter radial spray pattern is supplemented by a straight end spray for such cases where lumen treatment of quadrants is desired at the same time that targeted spray is needed for lesions or specific tissue. This is accomplished by the addition preformed tip of a Pebax extrusion or a molded polymer or cast metal that is adhered to the tip of the catheter. Such pre-formed tip controls the size of the end spray radius. The diameter can vary from 0.010 inches to full inner diameter of the catheter shaft. The current typical diameter shaft of the preferred embodiment is 0.061 inches. In alternate embodiments the distal end of the catheter may be a preformed plastic tip (typically Pebax) with a specific geometry that allows for specific spray patterns other than those coming out of the catheter shaft end (aka. straight spray). FIG. 13 also illustrates an optional radial spray configuration according to which catheter 271 is fitted with a spray pattern tip 272 that includes holes 273, 274, 275 of different sizes at different distance positions that allow for gradual spray across a specific distance of the catheter shaft 271. The hole patterns 273, 274, 275 may have dimensions that are between 0.005" to 0.050" in diameter. In this illustration, the hole at the distal end of the catheter 276 for straight spray may or may not be there and may have a diameter that is different from the rest. The diameter of hole 276 may have a range or 0.020" to 0.085 inches. The construction of this tip may be achieved via drilling of the different hole sizes, fusing or adhering a preformed and predrilled tip or insert molded via micromolding techniques.

Figure 14:
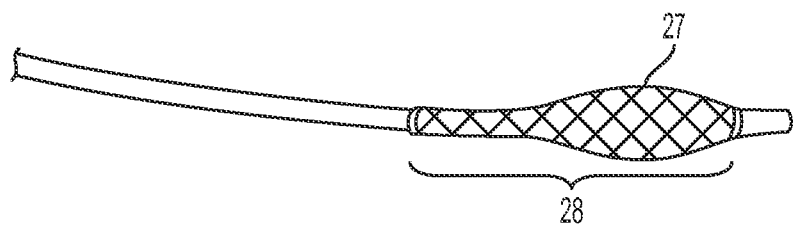
FIG. 14 shows an embodiment of the invention in which a mesh is arranged over the radial spray area directly to help diffuse and center such radial spray.

FIG. 14 shows an embodiment of a radial spray catheter where the self-centering mechanism is a cobalt chrome mesh basket 27 created out of a circular braid. The material can also be stainless steel wire or a polymeric molded process mesh. The main difference is that this centering basket is over the spray area 28 to create a well dispersed spray. In such case the mesh can be designed to be a visual aid for centering. The goal here is not necessarily to expand the mesh to touch all tissue, but instead to allow the basket to disperse the cryo spray more evenly in the spray treatment lumen.

Figure 15:
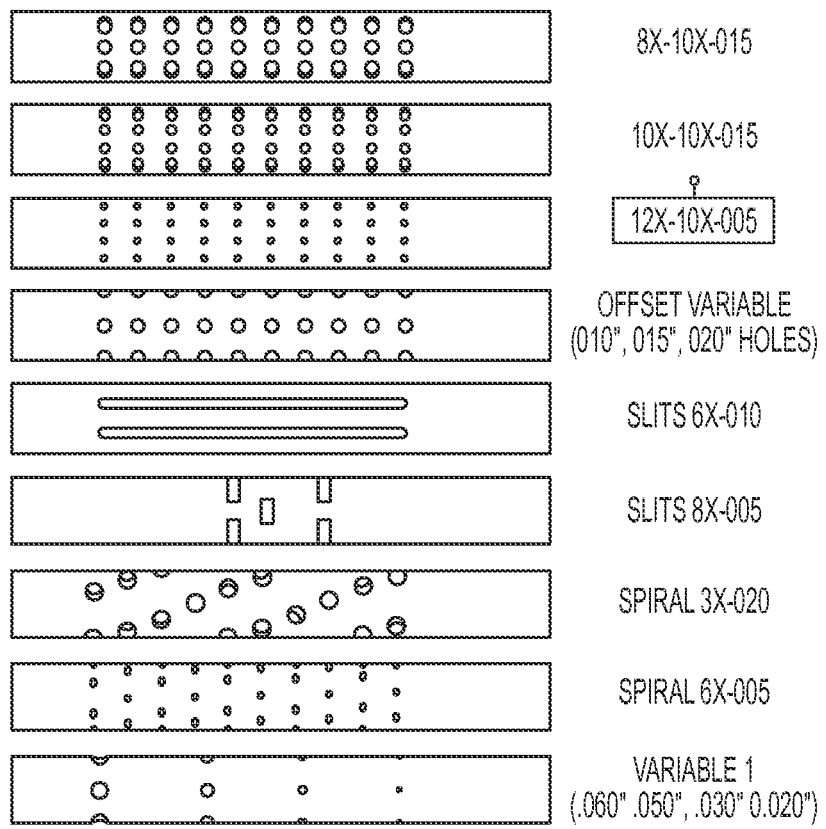
FIG. 15 shows various hole patterns of radial spray designs

FIG. 15 shows a fenestrated radial spray pattern illustration of different types of sprays attainable in the spray pattern area. The patterns from top to bottom demonstrate various hole patterns consisting of varying numbers of rows, varying hole sizes, number of holes per row, number of slits instead of rows, separation between holes, spiral hole patterns around the circumference, and variable hole patterns to compensate flow along the length of shaft. Slits can either be vertical or horizontal with respect to the shaft length. Individual hole sizes can vary from Outer Diameter to Inner Diameter. The holes can also be made at an angle within the wall thickness of the tube to direct spray in various directions.

Figure 16:
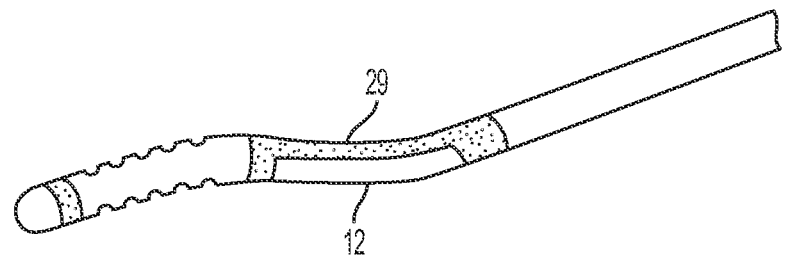
FIG. 16 shows an embodiment of the invention including an S-curve centering feature on the radial spray catheter containing an axial marker line that aids in visual positioning of such S-curve with respect to centering of such offset to the scope centerline

FIG. 16 is an isometric view of the catheter with an S-curve centering feature built into its distal tip shape. It shows the bend 12 and the alignment line 29 that is the feature used to visually align the catheter with respect to the scope working channel offset.

Figure 17:
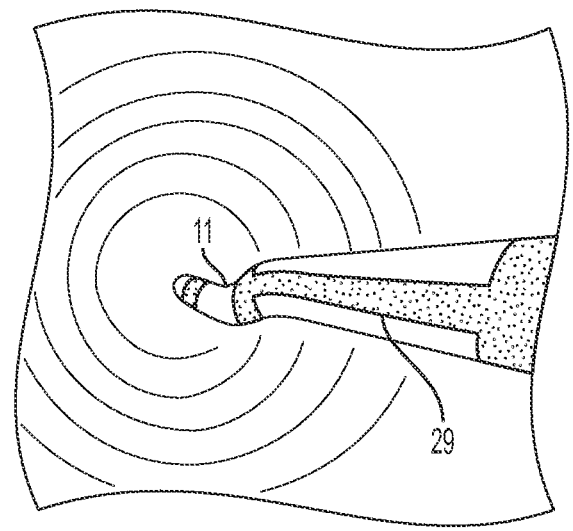
FIG. 17 shows an S-curve centering feature and axial line as viewed by the scope optics during use.

FIG. 17 shows the S-curve 12 as seen through the scope 20 visualization system. The method of use is to target the area to be treated by locating the catheter section 11 between the marking bands, then rotating the catheter axially until the axial line 29 is visible and horizontal in the line of vision. At this point the catheter tip is relatively centered with the scope 20 centerline. This axial line is typically created via a pad printed or laser marking process.

Not shown is a thermocouple wire construction within the catheter assembly that may be integrated outside of the proximal coil or hypotube construction. In addition, the thermocouple wire may be integrated into the braiding of the polymeric distal shaft or run along the outer diameter of such shaft. The thermocouple may connect to the console via a set of contacts within the console bayonet housing. The distal tip of the catheter is located within 3 cm of the tip and is also laser welded. Multiple thermocouple wires can be run along the shaft to create redundancy or report multiple catheter length locations. The typical wires used are copper and constantan.

According to a further embodiment the catheter may be fitted with a temperature sensing probe attached to the distal end of the catheter. This is achieved by laying at least two wires longitudinally or in a coil pattern prior to the outer layer of polymer laminated onto the catheter outer layer. If the wires are thermocouple wires, then they can be terminated into a thermocouple. Alternatively, a cryogenic thermistor can be attached to the distal end of the catheter. Such thermistor can then be encapsulated via conductive epoxy and a polymeric sleeve. Then the thermistor can be used to monitor both the temperature at the end of the catheter tip as well as the treatment area for both freezing and thawing temperature monitoring.

Figure 24:
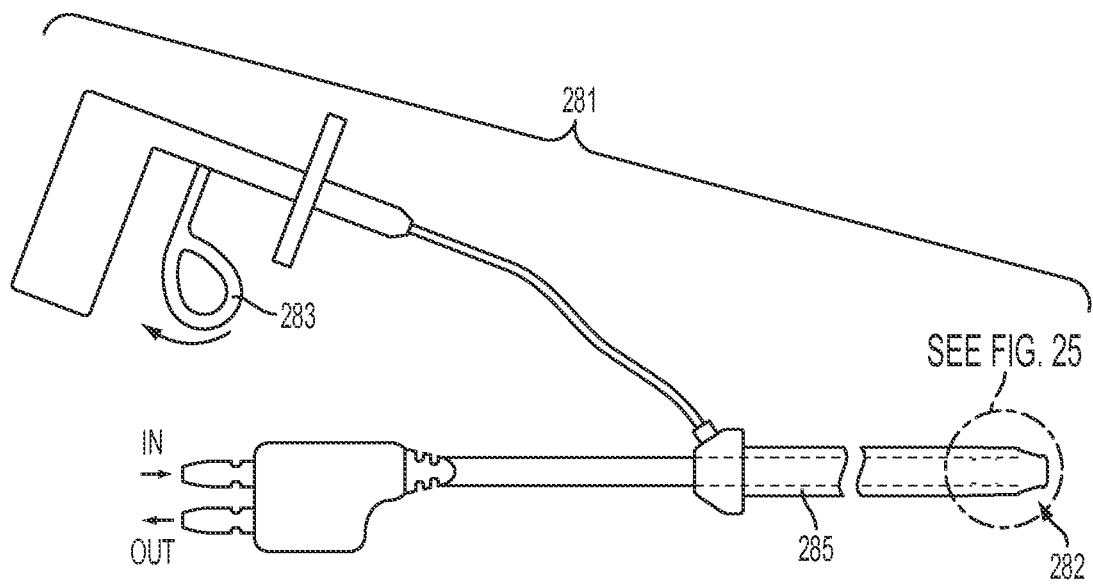
FIG. 24 shows a cryogen recirculating catheter according to an embodiment of the invention.

According to yet a further embodiment, there is provided a dual lumen, lumen-within-lumen catheter construction, see, e.g., FIG. 24. Such construction provides a cryospray catheter that can be precooled via the recirculation of fluid all the way to its distal end. The precooling is either achieved by the console control or the user's input command (like via a foot pedal). The cryospray catheter 281 contains a valve or shutter 282 that is then engaged either via the console control or the user. FIG. 24 describes the trigger type mechanism 283 that is engaged by the user for the duration of the spray to the treatment site. The mechanism 283 can be spring loaded to allow it to retrieve to the close position after treatment time is done. The valve is mechanically connected remotely to the trigger mechanism 283 via an engagement wire 284 running along the length of the catheter shaft 285. The wire 284 is connected to a sliding sleeve so that when the trigger is engaged the sleeve slides back and opens up the elastomeric diaphragm as shown retracted in dashed lines. A failsafe to the valve 282 opening and closing is the user can depress the console flow control that stops the recirculation along the catheter shaft 285 if the mechanical trigger fails to immediately retract due to freezing issues. The catheter shaft consists of dual lumens with an input and an output port for the path of recirculation.

Figure 25:
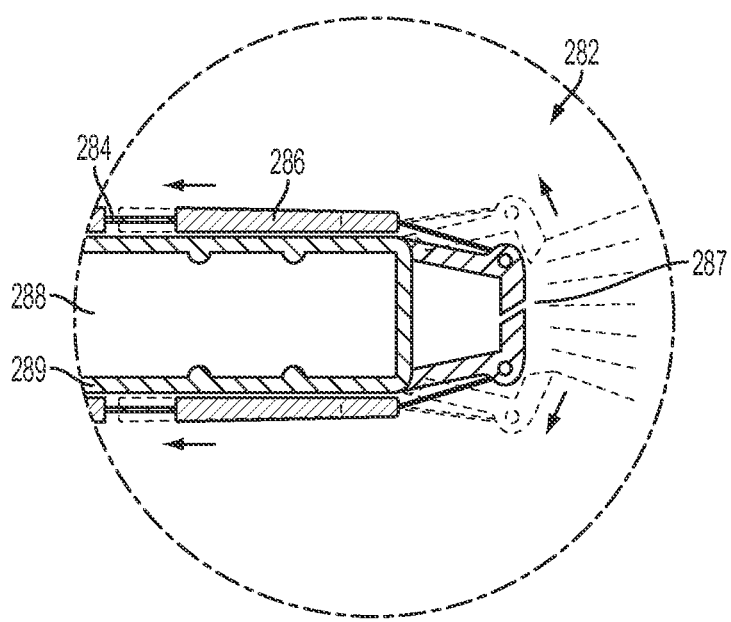
FIG. 25 is a close-up of the distal tip of the catheter shown in FIG. 24.

In FIG. 25, the recirculation path is shown via an inner lumen 288 that is surrounded by an outer lumen 289 which returns the dual phase fluid flow back to the console for recollection. Holes on the inner lumen 288 allow for this to occur.

Figure 23:
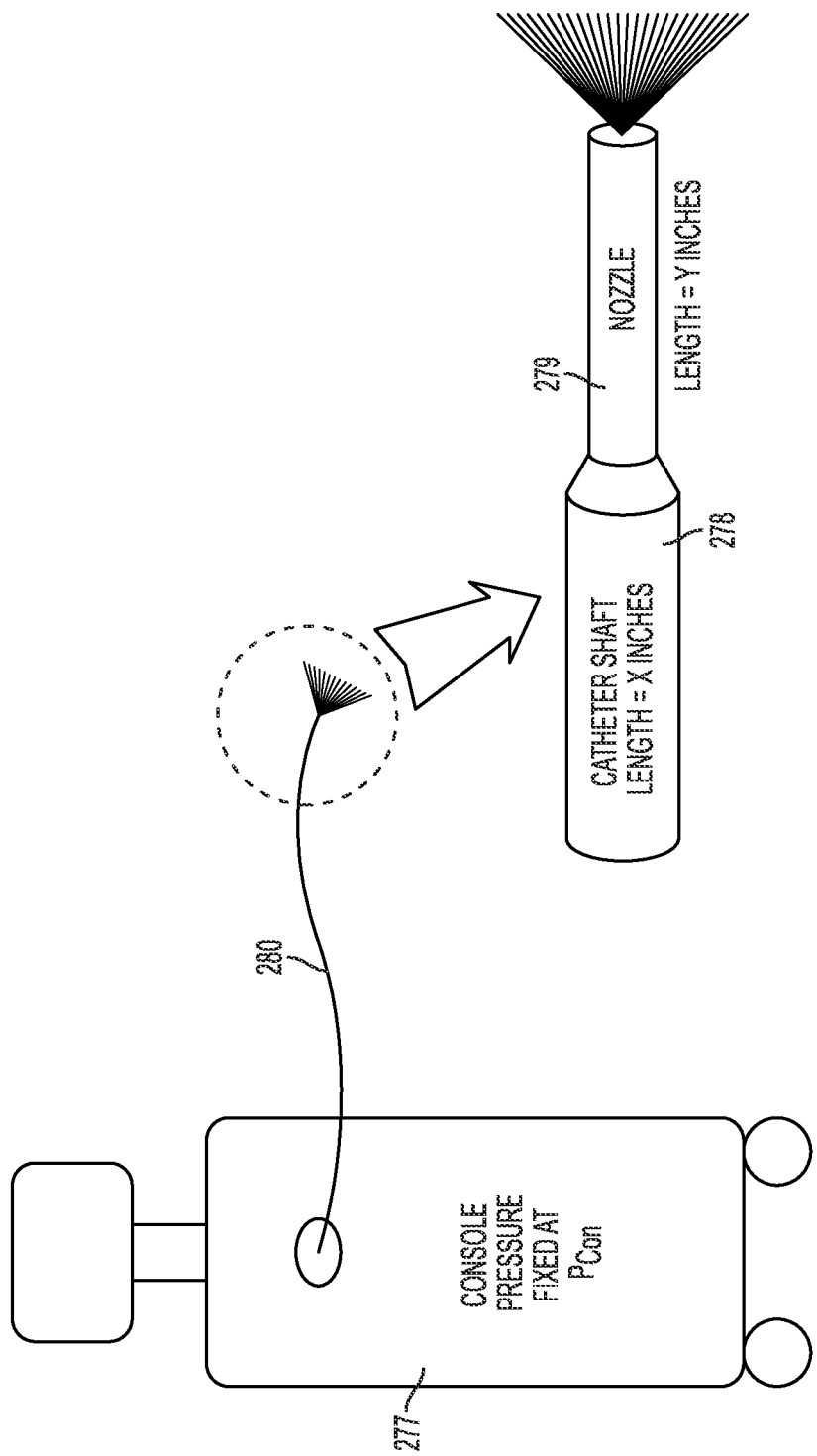
FIG. 23 is an illustration of an embodiment of the invention in which the catheter tip is fitted with a nozzle.

In yet another alternate embodiment, the control of the cryospray is achieved through a nozzle flow created by shafts of a certain length and diameter size, previously referred to as "nozzling." FIG. 23 demonstrates how the pressure of the console 277 may remain constant, but the combination of catheter shaft 278 and nozzle 279 are used to throttle the output flow at the distal end of the catheter 280 with a specific output flow. The nozzle 279 length can have a range of 0.050 inches to 48 inches in length and an inner diameter of 0.030 to 0.080 inches. Likewise the catheter shaft 278 of this construction can have a range of 1.5 inches to 90 inches when coupled with the nozzle construction. The catheter shaft can have an inner diameter range of 0.30 inches to 0.125 inches. More than one nozzle can be created along the catheter shaft length.

Vent Tube

Figure 18:
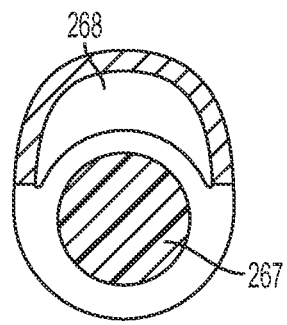
FIG. 18 is an illustration of the front view of a vent tube according to one embodiment of the invention.
Figure 19:
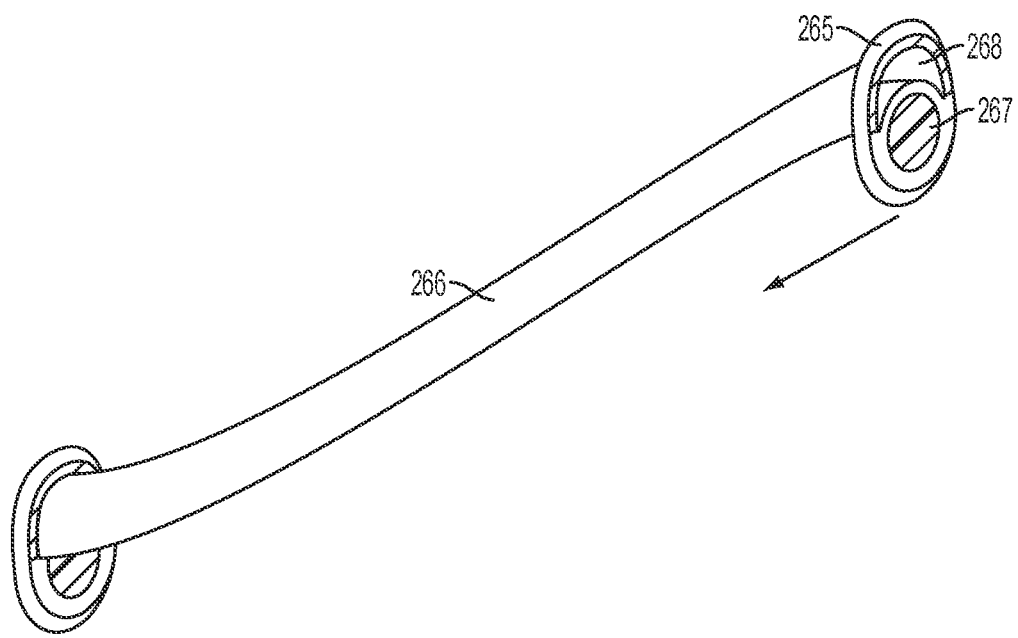
FIG. 19 is a perspective side view of the vent tube shown in FIG. 18.
Figure 20:
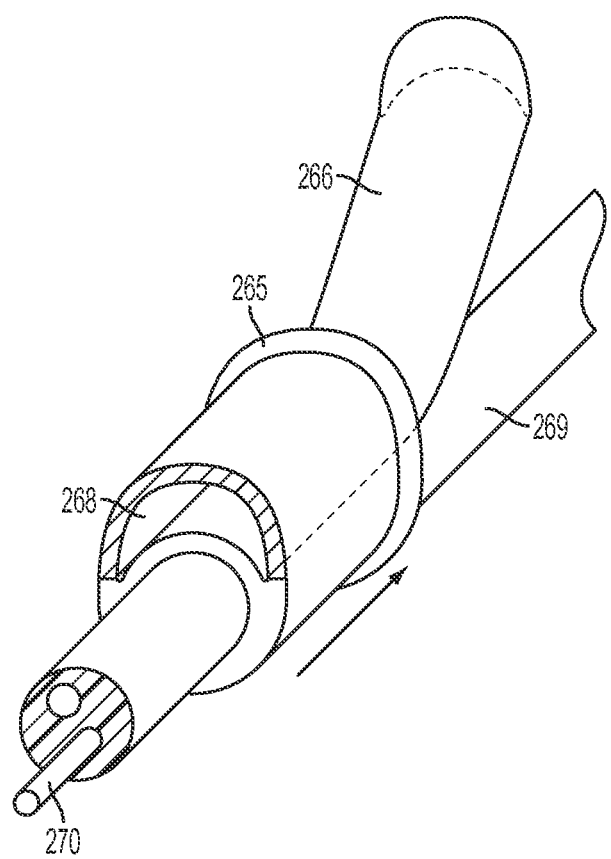
FIG. 20 is a perspective view of the vent tube shown in FIGS. 18 and 19, mated with a scope.
Figure 21:
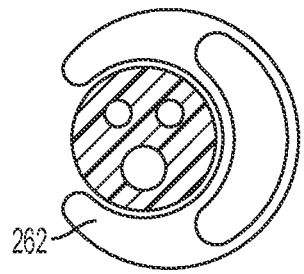
FIG. 21 is a front view of a vent tube according to another embodiment of the invention, together with the front face of a scope with which it is mated.
Figure 22:
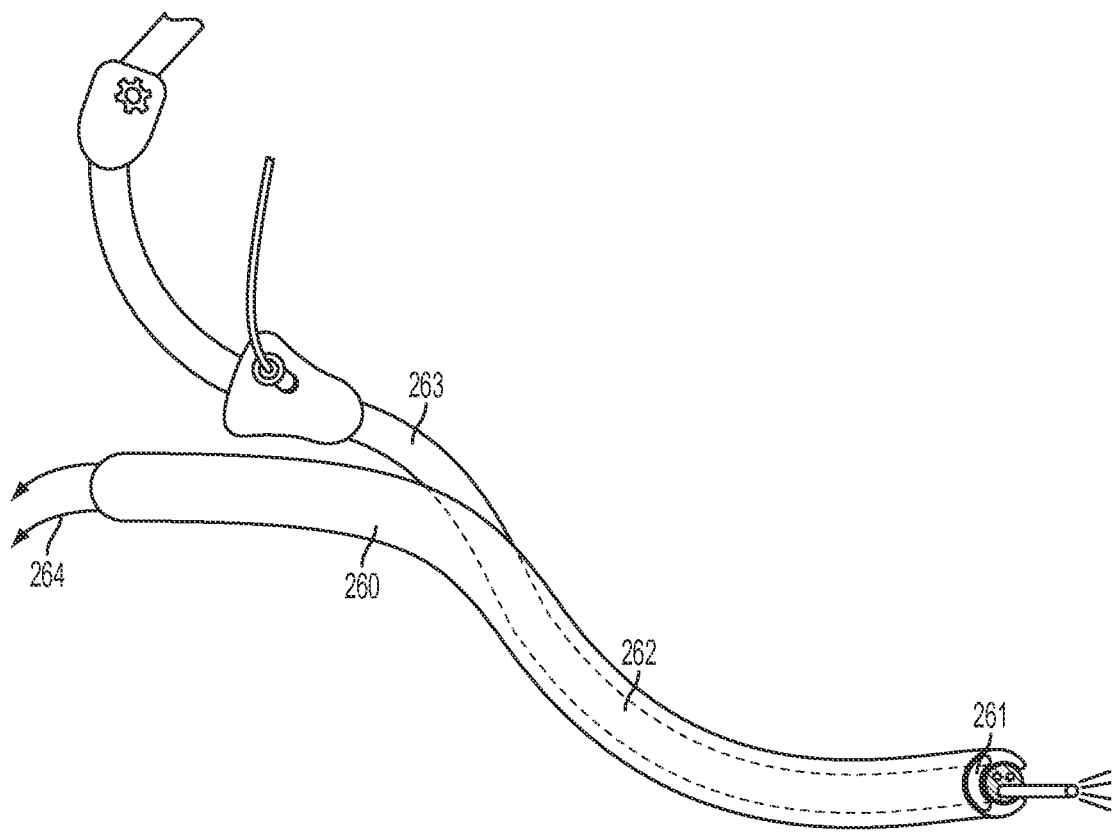
FIG. 22 is a perspective view of the vent tube and scope shown in FIG. 21.

The diameter of the area through which gas vents passively must be adequate to ensure organ or body cavity distention does not occur. Passive venting may be used with a vent tube when spraying proximal to a resistor where the lumen is patent (open), or when the treatment area is open to atmospheric pressure (e.g., dermatological or open surgery). A lumen sizing device (e.g. stent sizer) may be used to measure the lumen to aid in selection of vent tube size. The greater the vent area, the lower the pressure. The vent tube can be a separate tube used strictly for venting gas and creates a round vent area. The vent tube can also provide an annular vent area where the scope passes through the center of the tube. The distal end of the passive venting tube should be placed in an unobstructed cavity near the procedure area if area is not sufficiently open to atmospheric pressure. If used, the proximal end of the passive venting tube should be positioned outside the body where the pressure is atmospheric. In FIGS. 21 and 22 the vent tube 260 takes the shape of sleeve 262 with a lumen 261. Such sleeve 262 or grooved channel 262 can then be utilized to slip the scope 263 into it to allow for the scope insertion into the body cavity to be the placement mechanism. The vent tube is flexible enough that the functionality of the scope is not hindered. The tube ends with an open end 264 to vent to the atmosphere. FIGS. 18 through 20 show another version of the vent tube 266 with the sleeve 265 rolled up upon unpackaging, and a scope location opening 267, and a vent orifice 268. As shown in FIG. 20, it is unrolled over the scope shaft 269 and ready for use. FIG. 20 also shows the cryospray catheter 270 located out of the scope working channel. The vent hole 268 may be of dual vent lumen or single vent lumen construction which in turn supports both passive and active (suction) venting.

Egress Tube

Figure 29:
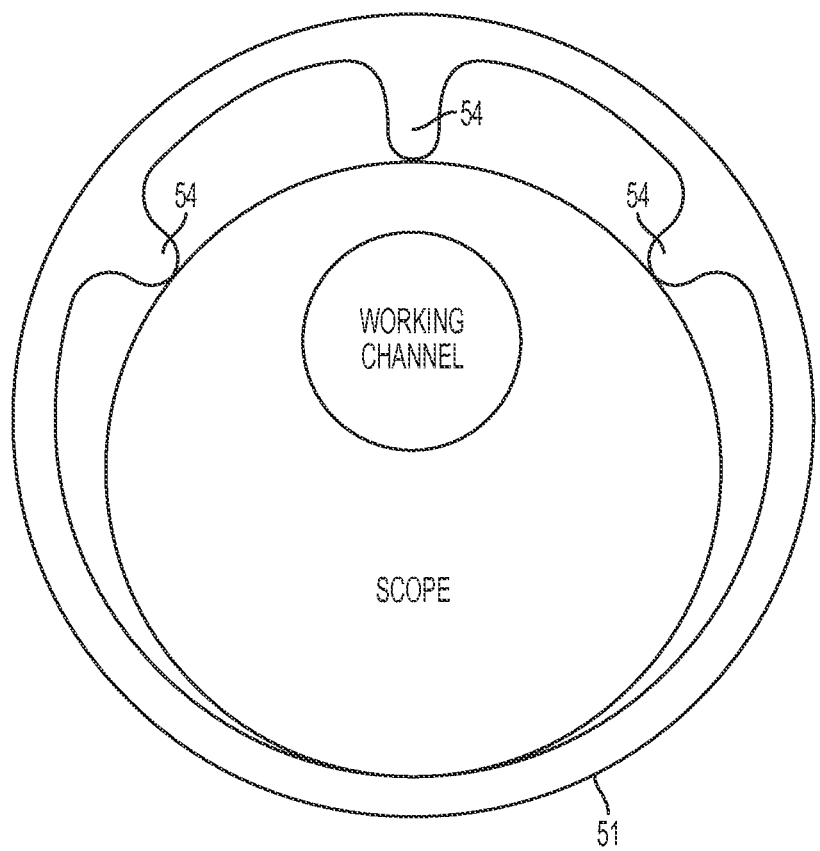
FIG. 29 shows a cross sectional view of an egress tube according to an embodiment of the invention, encapsulating an endoscope or bronchoscope.
Figure 30:
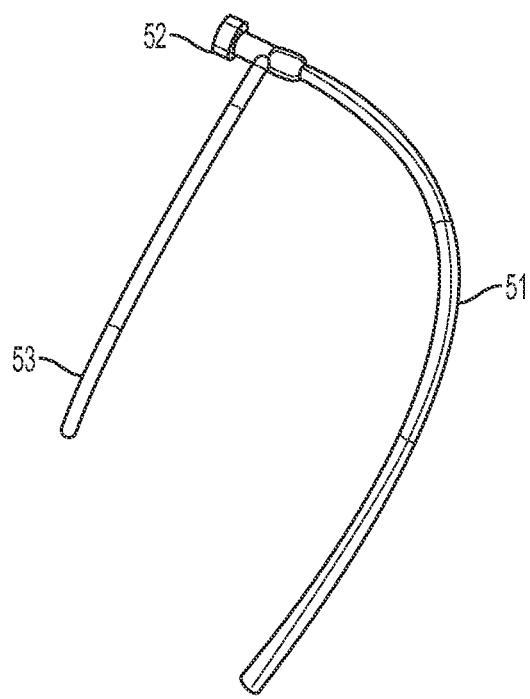
FIG. 30 is a side perspective view of an egress tube according to the invention.

FIGS. 29 and 30 show an egress tube according to an embodiment of the invention. According to a preferred embodiment, the egress tube 51 may be manufactured from a flexible polymeric material that can be easily extruded. It can have varying durometer (i.e., more flexible at distal tip for maneuvering). The exterior of the tube 51 may be coated for lubricity for ease of insertion or made of a lubricious material such as PTFE. According to the embodiment shown in FIG. 30, the egress tube may be connected to a gasket 52, preferably a large tuohy borst with a sideport, at the proximal end to lock the scope in position and to allow venting to a standard tube 53 for passive venting or active venting (connected to a suction pump). According to preferred embodiments of the invention, the exterior of the egress tube 51 may include finer measurement marks to provide guidance for placement of scope. According to further embodiments of the egress tube, it may be provided with a dedicated pressure lumen which can be constructed in a variety of ways (dual lumen extrusion, reflowing or adhesive of a separate extrusion, etc.).

According to the embodiment shown in FIG. 29, the interior surface of the egress tube 51 may be configured with ribs 54 (or, alternatively, rows of teeth or studs) for centering of the scope and creating the channels of egress. According to a preferred embodiment, the interior surface of the egress tube 51 has three ribs.

According to preferred embodiments of the egress tube of the invention, the scope is additionally insulated, the following features and advantages obtain:

completely encapsulates the scope for insulation;
affords a higher cross-sectional area for egress compared to prior art egress tube of the same size;
smallest outside diameter by utilizing ribs for preservation of egress area instead of material introduced between the scope and the egress areas;
allows for complete maneuverability of the scope by allowing for very small material wall thicknesses around the scope;
allows for treatment of tissue without the added management of a separate tube, as the egress is part of the scope assembly;
allows the scope to reach distal areas for treatment while maintaining vent egress up close;
ease of delivery into ET tube due to lubricious outer coating;
monitors pressure through a dedicated lumen.

Cryogen Decompression Tube

The cryogen decompression tube 132 on FIG. 1 aids evacuation of nitrogen gas from the treatment site. The cryogen decompression tube connects via supplied accessory connection tubing 167 to a disposable suction canister 169 on the front of the console. The dual lumens of the cryogen decompression tube are coupled to ports that provide both active (to the suction pump) and passive (direct to ambient) vent paths.

Figure 26:
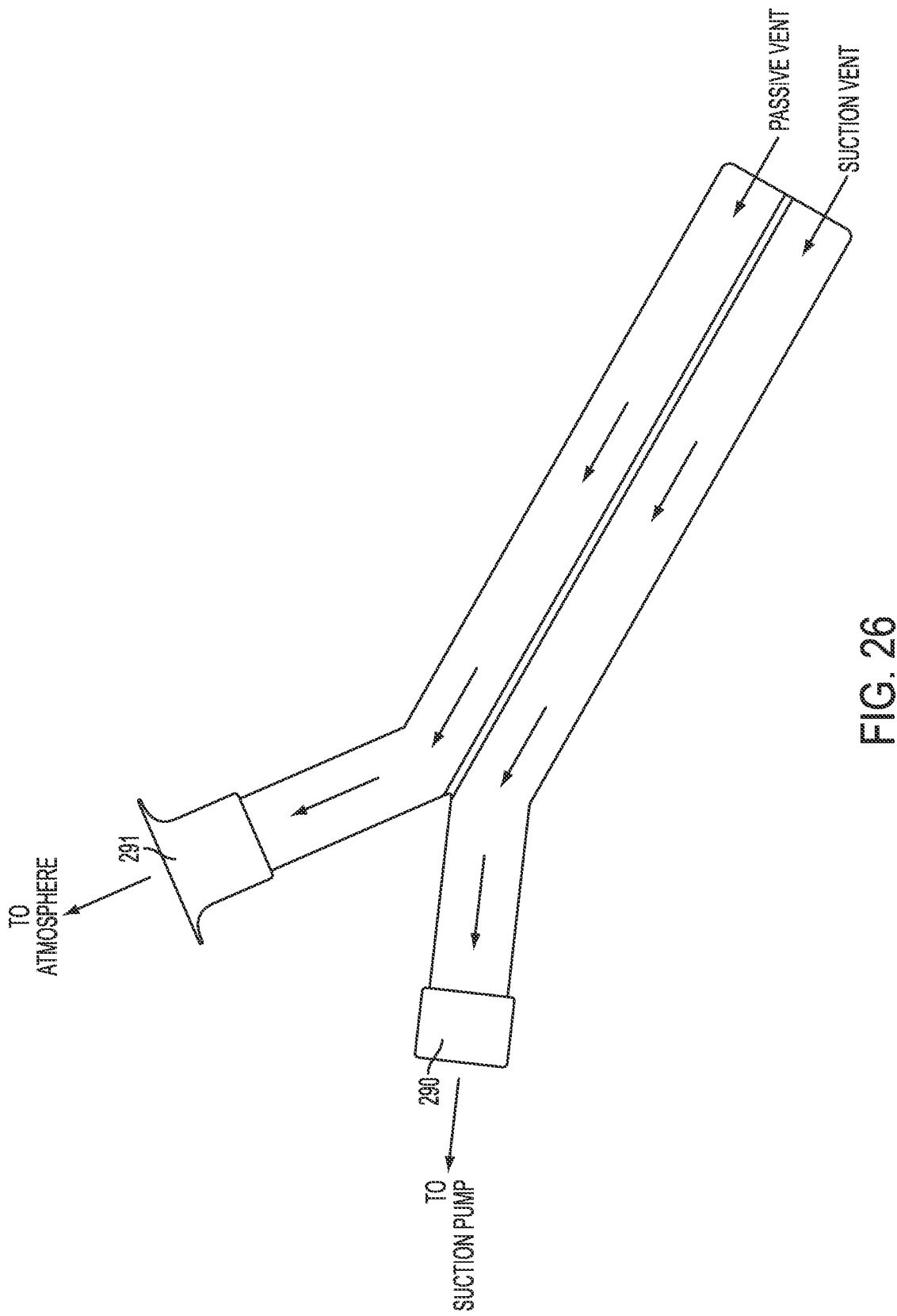
FIG. 26 is a side view of a dual lumen vent tube according to an embodiment of the invention.

The dual lumen cryodecompression tube may be of the form on FIG. 26, where each lumen is independently vented to either a suction pump tube connection or a passive open air connection 291. The passive venting may serve the function of vent during cryospray, but also the function of working channel to supplement the absence of a working channel if the catheter is inserted into the working channel of the scope. Such working channel can be used for tissue manipulation, forceps, biopsy, among other uses.

End Spray Diffuser

Figure 27:
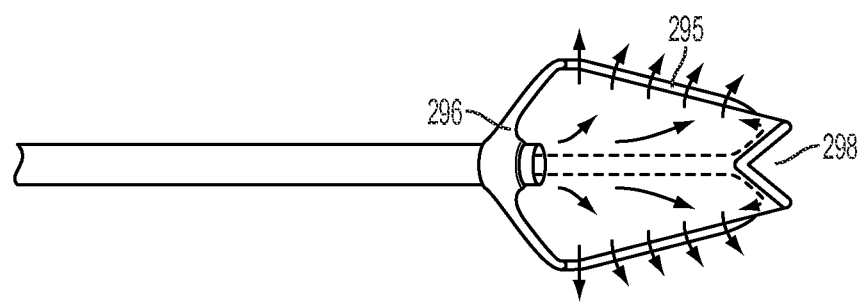
FIG. 27 shows an internal cross-section of a diffuser element according to an embodiment of the invention.
Figure 28:
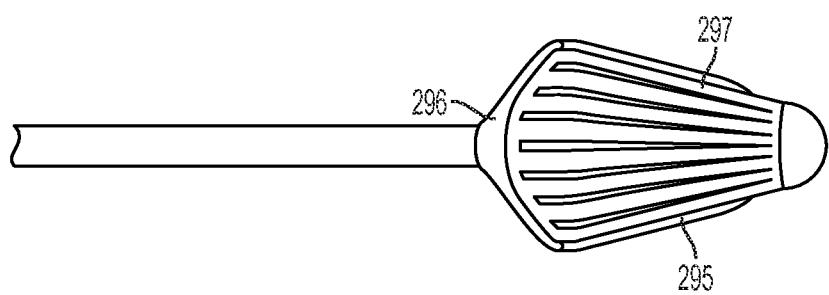
FIG. 28 shows an external side view of a diffuser element according to an embodiment of the invention.

When the catheter sprays out of the catheter distal tip it is described as straight spray. In the alternate embodiment illustrated in FIG. 28, the liquid nitrogen may be broken down into small droplets via a diffuser 295 or filter to allow for a very even spray pattern and avoid cold spots of spray pattern. The diffuser 295 may be constructed of filter paper, a grating patterned polymer, a metal or plastic mesh basket or laser cutting methods on the shaft itself to pattern it with very small holes. In such embodiment, the catheter ends in a cap 296 that contains small longitudinal cuts 297 that provide for controlled spray to exit as it initially hits a bounce plate 298 on FIG. 27. The bounce plate 298 is of a conical shape and helps distribute the spray evenly all around the diffuser 295 and cap 296.

Heavy Liquid and Light Gas Diverter Tube

Figure 31:
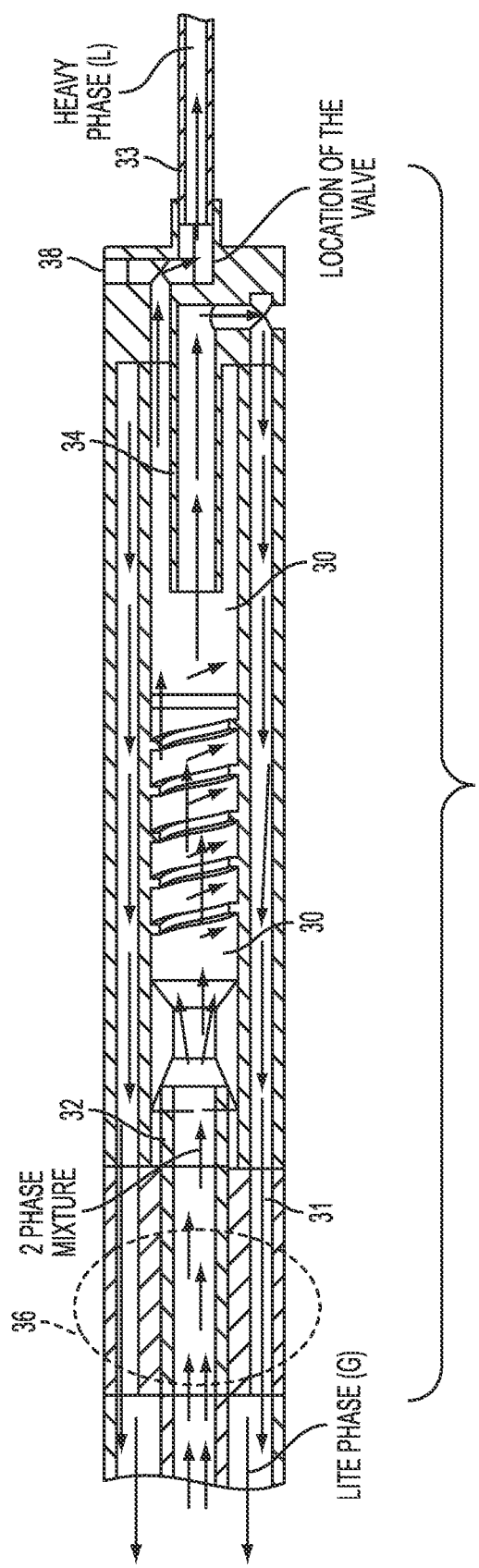
FIG. 31 shows an embodiment of the invention including a cyclone tube separator.
Figure 33:
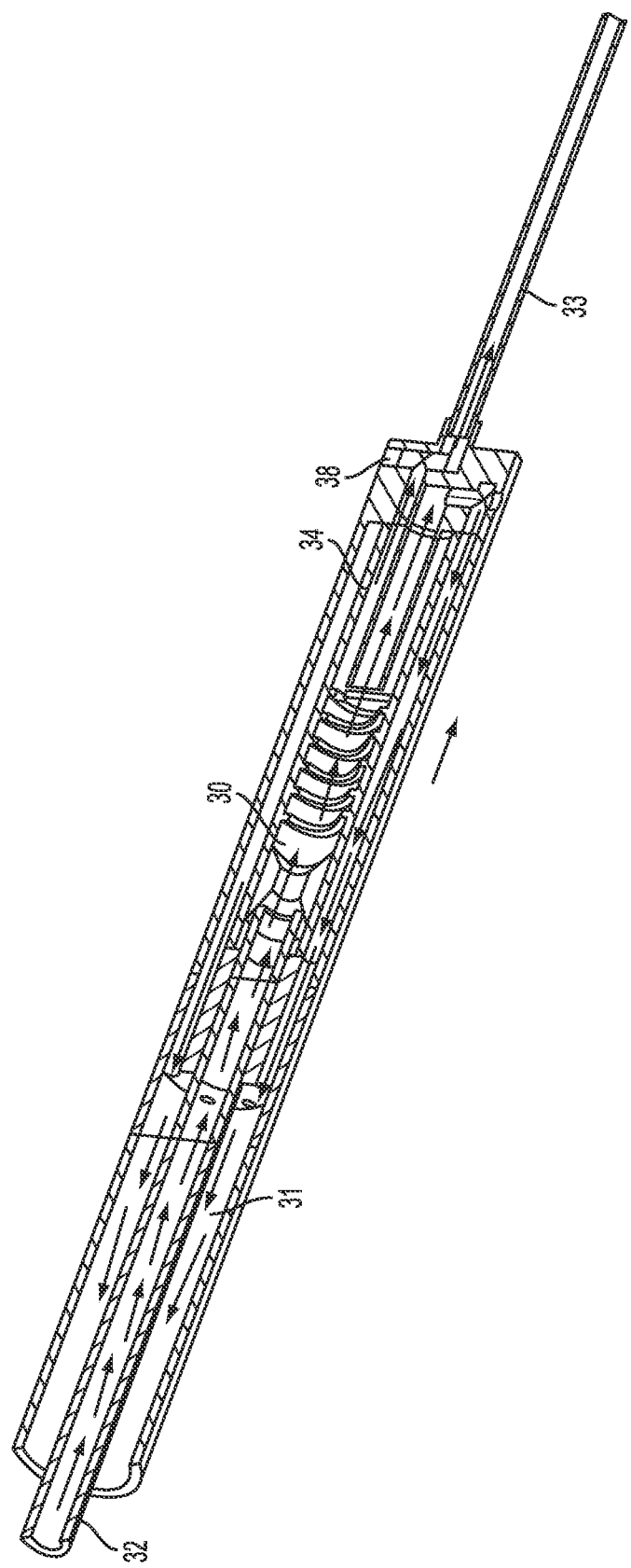
FIG. 33 is an isometric perspective of the cyclone tube manifold assembly at the distal shaft exit point showing the open and close valve area for effecting delivery of cryogen spray to the distal end.

FIG. 31 is a side perspective and FIG. 33 is an isometric view that shows a cyclone tube separator assembly 37 as it demonstrates the flow of liquid cryogen along the outer edges of the cyclone tube 30 and the cryogen gas is concentrated on the center part of the tube 30. The concentrated the cooling power of the liquid is directed to the distal shaft 33, while the gas portion of the cryogen is vented along the length of the proximal shaft 32 via a return jacket to create both a cooling effect on its surrounding air as well as an insulative layer of cryogenic gas flow. The cyclone tube 30 of the preferred embodiment is a cyclo-uniliner of quartz construction. Other embodiments may utilize other types of phase separation device for the cyclone tube. The cyclone tube aids in the separation of the heavier liquid from the lighter gas as the fluid travels through the cyclone tube. Spray is thus phase separated in the cyclone tube 30. The cyclone tube 30 of an alternate embodiment is a specialty tube that is formed via a casting, molding or machining process. The preferred embodiment utilizes a cyclone tube of quartz construction and is encased in a manifold assembly 37 that contains the gas funneling and orifices needed for fluid pathways. The gas center is redirected into an outer lumen 31 of the proximal portion of the catheter. The gas then exits near the bayonet into the cryospray console body for safety. The proximal tube 32 is constructed of a hypotube or polymeric shaft for the cryogen path into the cyclone tube, the outer lumen return jacket 31 concentric to the hypotube is an polymeric tube. The return jacket polymeric tube runs into the connector housing which then vents into the console. The outer edge of the cyclone tube exits into a nozzle that receives the distal shaft 33. The distal shaft then has the mostly liquid output with greater cryo cooling power. The return jacket and the hypotube form a coaxial double-pipe counter-flow heat exchanger 36.

Figure 32:
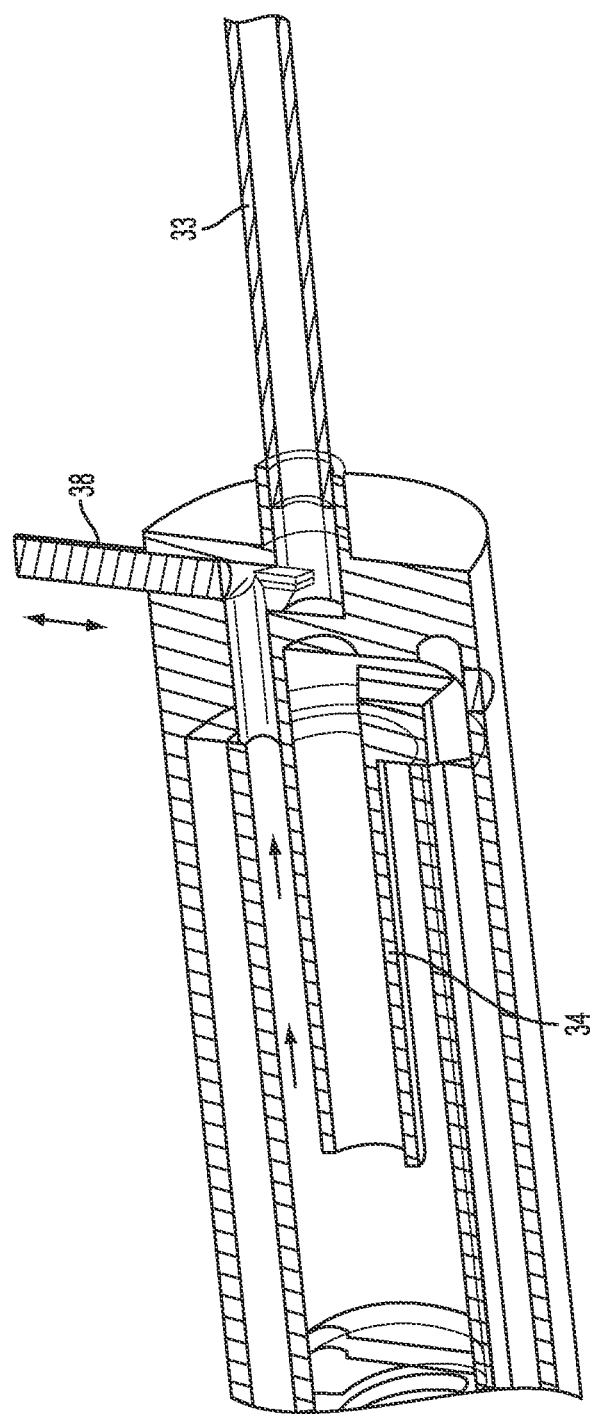
FIG. 32 is a side perspective of a cyclone tube construction assembly with a proximal shaft entry and a distal shaft exit points. A manifold surrounds the cyclone tube for redirection of fluid flow and flow control.

FIG. 32 shows the front end detail of the phase separator as equipped with a valve plug 38 that in the closed position would redirect the entire flow into the return jacket and heat exchanger section of the catheter and prevent any flow into the distal end of a catheter. This mode of operation would allow to precool section of the catheter between the console and phase separator and when the valve 38 is open, liquid enhanced spray can be injected into the distal portion 33 of the catheter.

The separator 37 may work without the cyclone to precool the proximal end 32 of the catheter. In this embodiment, only the fluid manifold portion of the separator 37 is used and the spray is partially redirected into the return jacket to prevent the spray flow inside the hypotube from excessive heat losses. The valve plug 38 can again be employed to interrupt the flow through the distal end 33 of the catheter during the precooling stage.

What is claimed:

1. A catheter for use with an endoscope comprising a multilayer construction for delivering low pressure cryogen spray to a treatment area, wherein said catheter comprises a proximal end configured to connect to a cryospray apparatus, and an open-ended distal end configured for the output of cryogen spray, said distal end having a blunt tip geometry and a pre-formed curve, whereby a central axis of the distal end outside of the endoscope during use is co-axial with a central axis of the endoscope, wherein said catheter is configured to retroflex during delivery of the cryogen spray to the treatment area.

2. The catheter of claim 1, wherein said multilayer construction comprises a polyimide layer and a Pebax layer, said blunt tip geometry consisting of Pebax.

3. The catheter of claim 1, wherein said multilayer construction comprises a torque and flexure resistant metal braid.

4. The catheter of claim 1, wherein said multilayer construction comprises a flexure and kink resistant metal.

5. The catheter of claim 1, wherein said multilayer construction comprises a PTFE layer or doping disposed on a polyimide layer.

6. The catheter of claim 5, wherein a coefficient of friction of the PTFE layer or doping is lower than a coefficient of friction of polyimide or Pebax.

7. A catheter for delivering low pressure cryogen spray to a treatment area with an endoscope, comprising a proximal end configured to connect to a cryospray delivery apparatus, an open-ended distal end configured for the output of cryogen spray, said distal end comprising a blunt tip geometry, a nozzle and a pre-formed curve, whereby a central axis of the distal end outside of the endo scope during use is co-axial with a central axis of the endoscope, wherein said catheter is configured to retroflex during delivery of the cryogen spray to the treatment area.

8. The catheter of claim 7, further comprising a length of tubing extending between the proximal and distal ends, wherein an inner diameter of the tubing is constant.

9. The catheter of claim 7, further comprising a length of tubing extending between the proximal and distal ends, wherein an inner diameter of the tubing varies along its length.

10. The catheter of claim 7, further comprising multiple lumens extending between the proximal and distal ends, the catheter configured to fit within a working channel of the endoscope.

11. The catheter of claim 10, wherein the multiple lumens are configured to deliver, circulate, actively vent or passively vent a cryogen.

12. The catheter of claim 7, wherein said open-ended distal end comprises a formed or molded tip configured to provide a cryogen spray pattern selected from the group consisting of an expanded spray pattern, a contracted spray pattern, a dispersed spray pattern and a diffused spray pattern.

13. The catheter of claim 7, wherein said open-ended distal end comprises a distal junction comprising a cryogen delivery lumen and a cryogen return lumen.

14. The catheter of claim 7, wherein said open-ended distal end includes a valve configured to be actuated remotely.

15. A catheter for delivering low pressure cryogen spray to a treatment area with an endoscope, comprising: a proximal end configured to connect to a cryospray apparatus, a pre-formed curve, whereby a central axis of a distal end of the catheter outside of the endoscope during use is co-axial with a central axis of the endoscope, and a multiple lumen output configured for cryogen circulation between the proximal and distal ends, the multiple lumen output comprising a cryogen input lumen and a cryogen output lumen, wherein said catheter is configured to retroflex during delivery of the cryogen spray to the treatment area.

16. The catheter of claim 15, wherein said proximal end is configured to connect to a cryogen delivery lumen and a cryogen return lumen.

17. A cryospray catheter for use with an endoscope comprising:
    a proximal metal interface bayonet configured to connect to a cryospray console;
    a plastic cover configured to interface with the cryospray console and bayonet;
    an insulating sheath distributed over a proximal portion of the cryospray catheter;
    a proximal tube with a first diameter; and
    a distal tube with a second diameter less than the first diameter and a pre-formed curve, whereby a central axis of the distal tube outside of the endoscope during use is co-axial with a central axis of the endoscope, wherein the cryospray catheter is configured to retroflex during delivery of a cryogen spray from the cryospray console through the proximal and distal tubes.

18. The cryospray catheter of claim 17, wherein the proximal tube comprises metal hypotube, ranging from 24 to 75 inches wherein a proximal portion of the metal hypotube is less flexible than a distal portion of the metal hypotube; and
    wherein said cryospray catheter further comprises an outer polymeric layer configured to form a fluid-tight lumen about at least a portion of the proximal tube.

19. The cryospray catheter of claim 17, wherein the proximal tube comprises a metal wire formed into a coil; and
    wherein said cryospray catheter further comprises an outer polymeric layer distributed over at least a portion of the proximal tube to provide a fluid-tight seal.

20. The cryospray catheter of claim 17, wherein the distal tube comprises a polyimide and braid construction.

21. The cryospray catheter of claim 17, wherein the distal tube comprises a metal hypotube construction.

22. The cryospray catheter of claim 17, wherein the distal tube comprises metal wire formed into a coil.

23. The cryospray catheter of claim 17, wherein the distal tube includes a single-end hole configured to form a spray pattern.

24. The cryospray catheter of claim 17, wherein the distal tube includes a plurality of radially-distributed fenestrations configured to form a spray pattern.

25. The cryospray catheter of claim 24 wherein the distal tube includes at least one marking band at each end of the radially-distributed fenestrations.

26. The cryospray catheter of claim 24, wherein the distal tube includes an occluded atraumatic tip configured to force a cryogen spray out of said radially-distributed fenestrations.

27. The cryospray catheter of claim 17, further comprising a temperature sensing probe at a distal end of the distal tube.

28. The cryospray catheter of claim 17, the distal tube further comprising a centering feature.

29. The cryospray catheter of claim 28, further comprising an axial marking configured to indicate an orientation of the centering feature.

30. The cryospray catheter of claim 17, further comprising a nozzle junction between said proximal tube and said distal tube.

31. The cryospray catheter of claim 30 wherein said nozzle junction comprises width extension wings configured to aid a user in positioning the distal tube.

32. The cryospray catheter of claim 30, wherein said nozzle junction includes:
   a cyclone tube configured to concentrate a cryogen spray;
   a vent tube concentric to the proximal tube and configured to direct expanding cryogen outside of the proximal tube; and
   a manifold configured to redirect the cryogen from outside the proximal tube to a treatment area.

33. The cryospray catheter of claim 32, further comprising a trigger configured to dispense a cryogenic fluid from the cryospray console through the proximal tube, the nozzle junction and the distal tube.

34. The cryospray catheter of claim 17, further comprising a self-centering catheter tip comprising a self-expanding spherical structure, a spring disposed within the self-expanding spherical structure, and an atraumatic tip configured to bond the self-expanding spherical structure to the spring.

35. The cryospray catheter of claim 34, wherein said self-expanding spherical structure includes at least one filament configured to form a spherical or oval shape.

36. The cryospray catheter of claim 34, wherein said self-expanding spherical structure comprises a chromium cobalt/stainless steel mesh.

37. The cryospray catheter of claim 34, wherein the self-centering catheter tip is expanded upon engaging a proximal trigger mechanism.

38. The cryospray catheter of claim 17, comprising an all-polymeric construction.

39. The cryospray catheter of claim 17, wherein said catheter is formed from a laser-cut metal hypotube.

40. The cryospray catheter of claim 17 where said proximal and distal tubes include an additive to improve thermal conductivity.

41. The cryospray catheter of claim 40 where such additive is silver.

42. The cryospray catheter of claim 40 where such additive is boron nitride.

43. The cryospray catheter of claim 40 where such additive is aluminum.

* * * * *